United States Patent
Schoenert et al.

(10) Patent No.: US 11,286,474 B2
(45) Date of Patent: Mar. 29, 2022

(54) ENZYME PRODUCTS

(71) Applicant: C-LEcta GmbH, Leipzig (DE)

(72) Inventors: Stefan Schoenert, Leipzig (DE);
Mathias Salomo, Leipzig (DE);
Thomas Schultchen, Leipzig (DE);
Andreas Vogel, Leipzig (DE); Sabrina Koepke, Leipzig (DE); Sebastian Bartsch, Leipzig (DE); Birgit Brucher, Leipzig (DE); Claudia Feller, Leipzig (DE)

(73) Assignee: C-LECTA GMBH, Leipzig (DE)

(*) Notice: Subject to any disclaimer, the term of this patent is extended or adjusted under 35 U.S.C. 154(b) by 0 days.

(21) Appl. No.: 16/682,511

(22) Filed: Nov. 13, 2019

(65) Prior Publication Data

US 2020/0140838 A1  May 7, 2020

Related U.S. Application Data

(63) Continuation of application No. PCT/EP2018/062476, filed on May 15, 2019.

(60) Provisional application No. 62/581,880, filed on Nov. 6, 2017, provisional application No. 62/506,357, filed on May 15, 2017.

(30) Foreign Application Priority Data

Nov. 8, 2017 (EP) .................................. 17200572
Mar. 16, 2018 (EP) .................................. 18162420

(51) Int. Cl.
| | | |
|---|---|---|
| C07K 1/34 | (2006.01) |
| C12N 9/22 | (2006.01) |
| C12N 15/52 | (2006.01) |
| C12N 9/12 | (2006.01) |
| C12N 15/70 | (2006.01) |
| C12N 9/52 | (2006.01) |

(52) U.S. Cl.
CPC .................. *C12N 9/52* (2013.01); *C07K 1/34* (2013.01); *C12N 9/12* (2013.01); *C12N 9/22* (2013.01); *C12N 15/52* (2013.01); *C12N 15/70* (2013.01); *C12Y 117/04001* (2013.01); *C12Y 204/01012* (2013.01); *C12Y 204/01015* (2013.01); *C12Y 301/03009* (2013.01); *C12Y 504/02002* (2013.01)

(58) Field of Classification Search
CPC ..... C12Y 301/31; C12Y 301/16; C12P 21/09; C12N 9/00; C07K 1/34
See application file for complete search history.

(56) References Cited

U.S. PATENT DOCUMENTS

| | | |
|---|---|---|
| 5,173,418 A | 12/1992 | Molin et al. |
| 8,706,939 B2 | 4/2014 | Ishikawa |
| 8,916,364 B2 | 12/2014 | Vogel et al. |
| 9,723,854 B2 | 8/2017 | Greiner-Stoeffele et al. |
| 10,238,731 B2* | 3/2019 | Ciaramella ............. A61K 39/39 |
| 2009/0123989 A1* | 5/2009 | Weggeman ............. C12N 7/00 435/239 |

FOREIGN PATENT DOCUMENTS

| | | |
|---|---|---|
| CN | 105985968 | * 10/2016 |
| CN | 106518956 A | 3/2017 |
| WO | 1987006939 A1 | 11/1987 |
| WO | 2008151807 A2 | 12/2008 |
| WO | 2012048865 A2 | 4/2012 |
| WO | 2015162064 A1 | 10/2015 |
| WO | 2016198660 A1 | 12/2016 |
| WO | 2016198665 A1 | 12/2016 |

OTHER PUBLICATIONS

European Patent Office, Extended European search report for European application EP18162420.6, dated Jun. 12, 2018.
GRAS-Notice No. 126; Immovase LLC, Alpha-Amylase Derived from Pseudomonas fluorescens Biovar I Expressing a Gene Encoding an Optimized Thermococcales Alpha-Amylase (Mar. 24, 2003).
L J Ausubel et al, "Production of CGMP-Grade Lentiviral Vectors", Feb. 1, 2012, p. 32-43, Retrieved from the Internet: URL:https://www.ncbi.nim.nih.gov/pmc/articles/PMC3374843/pdf/nihms377711.pdf (Feb. 1, 2012).
Martin et al., Uniprot Database, Rec. Name: Full=Sucrose synthase 1; Short=AtSUS1; EC=2.4.1.13; AltName: Full=Sucrose-UDP glucosyltransferase 1, UniProt01 Feb. 1996, retrieved from EBI accession No. UNIPROT: P49040 Database accession No. P49040, XP002781332 (Feb. 1, 1996).
P. C. Blainey et al., "Digital MDA for enumeration of total nucleic acid contamination", Nucleic Acids Research,vol. 39, No. 4, Nov. 11, 2010, p. e19-e19 (Nov. 11, 2010).
Richard R Burgess et al., "Use of Polyethyleneimine in Purification of DNA-Binding Proteins", Biochem. Biophys. Res. Commun. Biochim. Biophys. Acta J. Biol. Chem. Hoppe-Seyler's Z. Physiol. Chem. Biochemistry Biochemistry,vol. 208, Jan. 1, 1991 (Jan. 1, 1991), p. 3-10.
Takahashi Hirokazu et al., "Preparation of Phi29 DNA polymerase free of amplifiable DNA using ethidium monoazide, an ultraviolet-free light-emitting diode lamp and trehalose. Art. e82624", PLOS ONE,,vol. 9, No. 2, Jan. 1, 2014 (Jan. 1, 2014), p. 1-9.

(Continued)

*Primary Examiner* — Maryam Monshipouri
(74) *Attorney, Agent, or Firm* — Agris & von Natzmer, LLP; Joyce von Natzmer

(57) ABSTRACT

The invention relates to a process for the manufacturing and purification of recombinant enzyme products, in particular of food enzyme products and the use thereof. The invention particularly relates to a process for the processing of enzyme products from a microbial fermentation broth by methods of separation, enzymatic treatment and filtration procedures.

21 Claims, 1 Drawing Sheet
Specification includes a Sequence Listing.

(56) References Cited

OTHER PUBLICATIONS

Altschul S F, et al., "Gapped Blast and PSI-Blast: a New Generation of Protein Database Search Programs," Nucleic Acids Research, Oxford University Press, GB; vol. 25, Nr. 17, pp. 3389-3402 (1997).
EFSA Panel on Genetically Modified Organisms, Guidance on the risk assessment on genetically modified microorganisms and their products intended for food and feed use, EFSA Journal, vol. 9, No. 6, p. 2193 (2011).
Richman et al., Database accession No. AAR06912.1 (Dec. 28, 2004).
Altschul S et al., "Protein Database Searches Using Compositionally Adjusted Substitution Matrices", Febs J., vol. 272, pp. 5101-5109 (2005).
F. William Studier, Protein Expression and Purification, vol. 41, pp. 207-234 (2005).
NCBI, Database accession No. XP_004250485.1 (Aug. 8, 2018).
Tabata et al., Database accession No. NP_197583.1 (Feb. 14, 2019).

\* cited by examiner

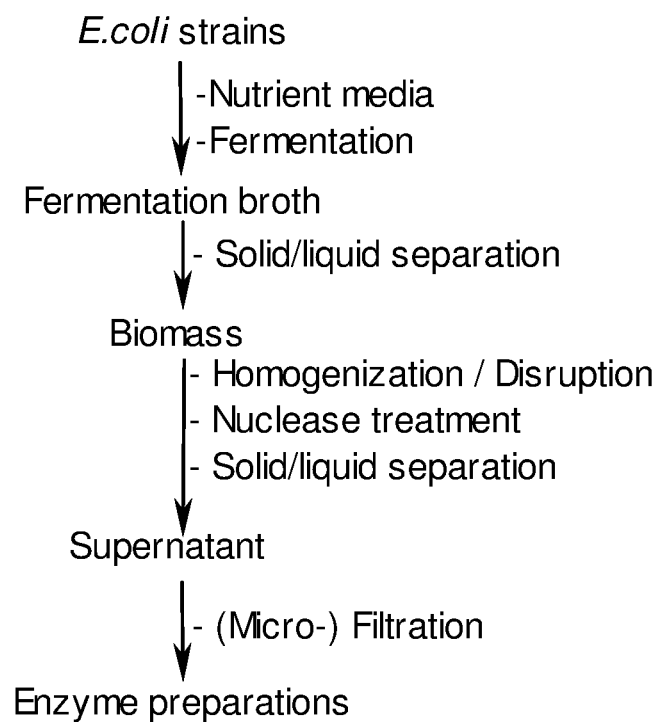

SEQUENCE LISTING

```
<160> NUMBER OF SEQ ID NOS: 5

<210> SEQ ID NO 1
<211> LENGTH: 245
<212> TYPE: PRT
<213> ORGANISM: Serratia marcescens
<220> FEATURE:
<221> NAME/KEY: MISC_FEATURE
<222> LOCATION: (1)..(245)
<223> OTHER INFORMATION: nuclease from Serratia marcescens

<400> SEQUENCE: 1
```

```
Asp Thr Leu Glu Ser Ile Asp Asn Cys Ala Val Gly Cys Pro Thr Gly
1               5                   10                  15

Gly Ser Ser Asn Val Ser Ile Val Arg His Ala Tyr Thr Leu Asn Asn
            20                  25                  30

Asn Ser Thr Thr Lys Phe Ala Asn Trp Val Ala Tyr His Ile Thr Lys
        35                  40                  45

Asp Thr Pro Ala Ser Gly Lys Thr Arg Asn Trp Lys Thr Asp Pro Ala
    50                  55                  60

Leu Asn Pro Ala Asp Thr Leu Ala Pro Ala Asp Tyr Thr Gly Ala Asn
65                  70                  75                  80

Ala Ala Leu Lys Val Asp Arg Gly His Gln Ala Pro Leu Ala Ser Leu
                85                  90                  95

Ala Gly Val Ser Asp Trp Glu Ser Leu Asn Tyr Leu Ser Asn Ile Thr
            100                 105                 110

Pro Gln Lys Ser Asp Leu Asn Gln Gly Ala Trp Ala Arg Leu Glu Asp
        115                 120                 125

Gln Glu Arg Lys Leu Ile Asp Arg Ala Asp Ile Ser Ser Val Tyr Thr
    130                 135                 140

Val Thr Gly Pro Leu Tyr Glu Arg Asp Met Gly Lys Leu Pro Gly Thr
145                 150                 155                 160

Gln Lys Ala His Thr Ile Pro Ser Ala Tyr Trp Lys Val Ile Phe Ile
                165                 170                 175

Asn Asn Ser Pro Ala Val Asn His Tyr Ala Ala Phe Leu Phe Asp Gln
            180                 185                 190

Asn Thr Pro Lys Gly Ala Asp Phe Cys Gln Phe Arg Val Thr Val Asp
        195                 200                 205

Glu Ile Glu Lys Arg Thr Gly Leu Ile Ile Trp Ala Gly Leu Pro Asp
    210                 215                 220

Asp Val Gln Ala Ser Leu Lys Ser Lys Pro Gly Val Leu Pro Glu Leu
225                 230                 235                 240

Met Gly Cys Lys Asn
                245
```

<210> SEQ ID NO 2
<211> LENGTH: 246
<212> TYPE: PRT
<213> ORGANISM: Artificial Sequence
<220> FEATURE:
<223> OTHER INFORMATION: SEQ ID NO:1 with one additional methionine at
      N-terminus

<400> SEQUENCE: 2

```
Met Asp Thr Leu Glu Ser Ile Asp Asn Cys Ala Val Gly Cys Pro Thr
1               5                   10                  15

Gly Gly Ser Ser Asn Val Ser Ile Val Arg His Ala Tyr Thr Leu Asn
            20                  25                  30

Asn Asn Ser Thr Thr Lys Phe Ala Asn Trp Val Ala Tyr His Ile Thr
        35                  40                  45

Lys Asp Thr Pro Ala Ser Gly Lys Thr Arg Asn Trp Lys Thr Asp Pro
    50                  55                  60

Ala Leu Asn Pro Ala Asp Thr Leu Ala Pro Ala Asp Tyr Thr Gly Ala
65                  70                  75                  80

Asn Ala Ala Leu Lys Val Asp Arg Gly His Gln Ala Pro Leu Ala Ser
                85                  90                  95

Leu Ala Gly Val Ser Asp Trp Glu Ser Leu Asn Tyr Leu Ser Asn Ile
```

```
                        100              105              110
Thr Pro Gln Lys Ser Asp Leu Asn Gln Gly Ala Trp Ala Arg Leu Glu
            115                 120                 125

Asp Gln Glu Arg Lys Leu Ile Asp Arg Ala Asp Ile Ser Ser Val Tyr
130                 135                 140

Thr Val Thr Gly Pro Leu Tyr Glu Arg Asp Met Gly Lys Leu Pro Gly
145                 150                 155                 160

Thr Gln Lys Ala His Thr Ile Pro Ser Ala Tyr Trp Lys Val Ile Phe
                165                 170                 175

Ile Asn Asn Ser Pro Ala Val Asn His Tyr Ala Ala Phe Leu Phe Asp
            180                 185                 190

Gln Asn Thr Pro Lys Gly Ala Asp Phe Cys Gln Phe Arg Val Thr Val
        195                 200                 205

Asp Glu Ile Glu Lys Arg Thr Gly Leu Ile Ile Trp Ala Gly Leu Pro
210                 215                 220

Asp Asp Val Gln Ala Ser Leu Lys Ser Lys Pro Gly Val Leu Pro Glu
225                 230                 235                 240

Leu Met Gly Cys Lys Asn
                245

<210> SEQ ID NO 3
<211> LENGTH: 808
<212> TYPE: PRT
<213> ORGANISM: Arabidopsis thaliana
<220> FEATURE:
<221> NAME/KEY: MISC_FEATURE
<222> LOCATION: (1)..(808)
<223> OTHER INFORMATION: sucrose synthase 1 from Arabidopsis thaliana
      (NCBI Reference Sequence: NP_197583.1)

<400> SEQUENCE: 3

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
                85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
    130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
```

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |

Thr Leu Arg Lys Ala Glu Glu Tyr Leu Ala Glu Leu Lys Ser Glu Thr
210                     215                     220

Leu Tyr Glu Glu Phe Glu Ala Lys Phe Glu Glu Ile Gly Leu Glu Arg
225                     230                     235                     240

Gly Trp Gly Asp Asn Ala Glu Arg Val Leu Asp Met Ile Arg Leu Leu
                        245                     250                     255

Leu Asp Leu Leu Glu Ala Pro Asp Pro Cys Thr Leu Glu Thr Phe Leu
                260                     265                     270

Gly Arg Val Pro Met Val Phe Asn Val Val Ile Leu Ser Pro His Gly
        275                     280                     285

Tyr Phe Ala Gln Asp Asn Val Leu Gly Tyr Pro Asp Thr Gly Gly Gln
290                     295                     300

Val Val Tyr Ile Leu Asp Gln Val Arg Ala Leu Glu Ile Glu Met Leu
305                     310                     315                     320

Gln Arg Ile Lys Gln Gln Gly Leu Asn Ile Lys Pro Arg Ile Leu Ile
                        325                     330                     335

Leu Thr Arg Leu Leu Pro Asp Ala Val Gly Thr Thr Cys Gly Glu Arg
                340                     345                     350

Leu Glu Arg Val Tyr Asp Ser Glu Tyr Cys Asp Ile Leu Arg Val Pro
        355                     360                     365

Phe Arg Thr Glu Lys Gly Ile Val Arg Lys Trp Ile Ser Arg Phe Glu
370                     375                     380

Val Trp Pro Tyr Leu Glu Thr Tyr Thr Glu Asp Ala Ala Val Glu Leu
385                     390                     395                     400

Ser Lys Glu Leu Asn Gly Lys Pro Asp Leu Ile Ile Gly Asn Tyr Ser
                        405                     410                     415

Asp Gly Asn Leu Val Ala Ser Leu Leu Ala His Lys Leu Gly Val Thr
                420                     425                     430

Gln Cys Thr Ile Ala His Ala Leu Glu Lys Thr Lys Tyr Pro Asp Ser
        435                     440                     445

Asp Ile Tyr Trp Lys Lys Leu Asp Asp Lys Tyr His Phe Ser Cys Gln
450                     455                     460

Phe Thr Ala Asp Ile Phe Ala Met Asn His Thr Asp Phe Ile Ile Thr
465                     470                     475                     480

Ser Thr Phe Gln Glu Ile Ala Gly Ser Lys Glu Thr Val Gly Gln Tyr
                        485                     490                     495

Glu Ser His Thr Ala Phe Thr Leu Pro Gly Leu Tyr Arg Val Val His
                500                     505                     510

Gly Ile Asp Val Phe Asp Pro Lys Phe Asn Ile Val Ser Pro Gly Ala
        515                     520                     525

Asp Met Ser Ile Tyr Phe Pro Tyr Thr Glu Glu Lys Arg Arg Leu Thr
530                     535                     540

Lys Phe His Ser Glu Ile Glu Glu Leu Leu Tyr Ser Asp Val Glu Asn
545                     550                     555                     560

Lys Glu His Leu Cys Val Leu Lys Asp Lys Lys Pro Ile Leu Phe
                        565                     570                     575

Thr Met Ala Arg Leu Asp Arg Val Lys Asn Leu Ser Gly Leu Val Glu
                580                     585                     590

Trp Tyr Gly Lys Asn Thr Arg Leu Arg Glu Leu Ala Asn Leu Val Val
        595                     600                     605

Val Gly Gly Asp Arg Arg Lys Glu Ser Lys Asp Asn Glu Glu Lys Ala
610                     615                     620

```
Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
            645                 650                 655

Leu Tyr Arg Tyr Ile Cys Asp Thr Lys Gly Ala Phe Val Gln Pro Ala
        660                 665                 670

Leu Tyr Glu Ala Phe Gly Leu Thr Val Val Glu Ala Met Thr Cys Gly
    675                 680                 685

Leu Pro Thr Phe Ala Thr Cys Lys Gly Gly Pro Ala Glu Ile Ile Val
690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
        755                 760                 765

Tyr Gly Phe Trp Lys His Val Ser Asn Leu Asp Arg Leu Glu Ala Arg
    770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 4
<211> LENGTH: 458
<212> TYPE: PRT
<213> ORGANISM: Stevia rebaudiana
<220> FEATURE:
<221> NAME/KEY: MISC_FEATURE
<222> LOCATION: (1)..(458)
<223> OTHER INFORMATION: UDP-glycosyltransferase 76G1 from Stevia
      rebaudiana (Genbank accession no. AAR06912.1)

<400> SEQUENCE: 4

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160
```

```
Phe Asp Glu Leu Gly Tyr Leu Asp Pro Asp Lys Thr Arg Leu Glu
            165                 170                 175

Glu Gln Ala Ser Gly Phe Pro Met Leu Lys Val Lys Asp Ile Lys Ser
        180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
        210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
            245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
            275                 280                 285

Glu Lys Asp Phe Leu Glu Ile Ala Arg Gly Leu Val Asp Ser Lys Gln
            290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
    450                 455

<210> SEQ ID NO 5
<211> LENGTH: 442
<212> TYPE: PRT
<213> ORGANISM: Solanum lycopersicum
<220> FEATURE:
<221> NAME/KEY: MISC_FEATURE
<222> LOCATION: (1)..(442)
<223> OTHER INFORMATION: beta-D-glycosyl crovetin beta-1,6-
      glycosyltransferase-like enzyme from Solanum lycopersicum (Genbank
      accession no. XP_004250485.1)

<400> SEQUENCE: 5

Met Ala Thr Asn Leu Arg Val Leu Met Phe Pro Trp Leu Ala Tyr Gly
1               5                   10                  15

His Ile Ser Pro Phe Leu Asn Ile Ala Lys Gln Leu Ala Asp Arg Gly
            20                  25                  30

Phe Leu Ile Tyr Leu Cys Ser Thr Arg Ile Asn Leu Glu Ser Ile Ile
```

```
            35                  40                  45
Lys Lys Ile Pro Glu Lys Tyr Ala Asp Ser Ile His Leu Ile Glu Leu
 50                  55                  60

Gln Leu Pro Glu Leu Pro Glu Leu Pro Pro His Tyr His Thr Thr Asn
 65                  70                  75                  80

Gly Leu Pro Pro His Leu Asn Pro Thr Leu His Lys Ala Leu Lys Met
                 85                  90                  95

Ser Lys Pro Asn Phe Ser Arg Ile Leu Gln Asn Leu Lys Pro Asp Leu
            100                 105                 110

Leu Ile Tyr Asp Val Leu Gln Pro Trp Ala Glu His Val Ala Asn Glu
        115                 120                 125

Gln Asn Ile Pro Ala Gly Lys Leu Leu Thr Ser Cys Ala Ala Val Phe
    130                 135                 140

Ser Tyr Phe Phe Ser Phe Arg Lys Asn Pro Gly Val Glu Phe Pro Phe
145                 150                 155                 160

Pro Ala Ile His Leu Pro Glu Val Glu Lys Val Lys Ile Arg Glu Ile
                165                 170                 175

Leu Ala Lys Glu Pro Glu Glu Gly Gly Arg Leu Asp Glu Gly Asn Lys
            180                 185                 190

Gln Met Met Leu Met Cys Thr Ser Arg Thr Ile Glu Ala Lys Tyr Ile
        195                 200                 205

Asp Tyr Cys Thr Glu Leu Cys Asn Trp Lys Val Pro Val Gly Pro
    210                 215                 220

Pro Phe Gln Asp Leu Ile Thr Asn Asp Ala Asp Asn Lys Glu Leu Ile
225                 230                 235                 240

Asp Trp Leu Gly Thr Lys His Glu Asn Ser Thr Val Phe Val Ser Phe
                245                 250                 255

Gly Ser Glu Tyr Phe Leu Ser Lys Glu Asp Met Glu Glu Val Ala Phe
            260                 265                 270

Ala Leu Glu Leu Ser Asn Val Asn Phe Ile Trp Val Ala Arg Phe Pro
        275                 280                 285

Lys Gly Glu Glu Arg Asn Leu Glu Asp Ala Leu Pro Lys Gly Phe Leu
    290                 295                 300

Glu Arg Ile Gly Glu Arg Gly Arg Val Leu Asp Lys Phe Ala Pro Gln
305                 310                 315                 320

Pro Arg Ile Leu Asn His Pro Ser Thr Gly Gly Phe Ile Ser His Cys
                325                 330                 335

Gly Trp Asn Ser Ala Met Glu Ser Ile Asp Phe Gly Val Pro Ile Ile
            340                 345                 350

Ala Met Pro Ile His Asn Asp Gln Pro Ile Asn Ala Lys Leu Met Val
        355                 360                 365

Glu Leu Gly Val Ala Val Glu Ile Val Arg Asp Asp Gly Lys Ile
    370                 375                 380

His Arg Gly Glu Ile Ala Glu Thr Leu Lys Ser Val Val Thr Gly Glu
385                 390                 395                 400

Thr Gly Glu Ile Leu Arg Ala Lys Val Arg Glu Ile Ser Lys Asn Leu
                405                 410                 415

Lys Ser Ile Arg Asp Glu Glu Met Asp Ala Val Ala Glu Glu Leu Ile
            420                 425                 430

Gln Leu Cys Arg Asn Ser Asn Lys Ser Lys
        435                 440
```

ENZYME PRODUCTS

CROSS REFERENCE TO RELATED APPLICATIONS

This application is a continuation of international application no. PCT/EP2018/062476, filed on May 15, 2018, which is incorporated herein by reference in its entirety and which claims the benefit of U.S. patent application Ser. No. 62/506,357, filed on May 15, 2017; U.S. patent application Ser. No. 62/581,880, filed on Nov. 6, 2017; and priority to European patent application no. 17 200 572.0, filed on Nov. 8, 2017; and European patent application no. 18 162 420.6, filed on Mar. 16, 2018.

INCORPORATION OF SEQUENCE LISTING

This application was filed electronically via EFS-Web and includes an electronically submitted sequence listing in .txt format. The .txt file contains a sequence listing entitled "3054-109_ST25.txt" created on Jan. 22, 2020, and is 20 kilobytes in size. The sequence listing in this .txt file is part of the specification and is hereby incorporated by reference herein in its entirety.

FIELD OF THE INVENTION

The invention relates to a process for the manufacturing and purification of recombinant enzyme products, in particular of food enzyme products and the use thereof. The invention particularly relates to a process for the processing of enzyme products from a microbial fermentation broth by methods of separation, enzymatic treatment and filtration procedures.

BACKGROUND OF AND INTRODUCTION TO THE INVENTION

The manufacturing of recombinant enzymes from microbial strains has been extensively described in the state of the art. *Escherichia coli* is a well-known expression host for recombinant enzymes from laboratory to industrial scale.

The manufacturing of enzyme products, in particular of enzyme products for use in food or pharma application, requires achievement of specific specification requirements for safe and authorized use of such enzyme products.

Due to regulatory demands an enzyme product that is intended to be used in food applications should be free of or reduced in recombinant DNA. Many enzymes cannot be secreted and therefore need to be expressed as intracellular enzyme. To release them from the expression host a cell disruption step is needed. This cell disruption is connected to the release of large amounts of DNA from the expression host. In case of a recombinant production process along with such DNA release also recombinant DNA is released. This recombinant DNA needs to be removed again.

GRAS Notice GRN No. 126 describes the manufacturing of an alpha-amylase enzyme preparation from *Pseudomonas fluorescens* Biovar I expressing a gene encoding a hybrid alpha-amylase derived from three microorganisms within the order Thermococcales. It is for use as an enzyme for the hydrolysis of edible starch to produce various starch hydrolysis products and to produce fermentable sugars for use in the production of distilled ethanol for alcoholic beverages.

Enzyme products derived from recombinant production are widely used in the food industry. Enzyme classes offered as enzyme products include, amongst others, enzymes belonging to the enzyme class groups consisting of oxidoreductases, transferases, hydrolases, lyases, isomerases, and ligases, and for example is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, or xylose isomerases. Specifically such enzyme products may be carbohydrate-modifying enzymes, such as glycosyl hydrolases, glycosyltransferases, polysaccharide lyases, carbohydrate esterases, amino acid, peptide or protein-modifying enzymes, such as aminotransferases, proteases and peptidases; and lipid modifying enzymes such as lipases or phospholipases.

Furthermore, food enzyme products are regularly used for the enzymatic conversion of certain substrates for the production of food ingredients, like certain di-, tri-, or oligo-saccharides. Such enzymatic conversion applications of enzymes are also referred to hereinafter as "downstream enzymatic conversions".

In order to meet the regulatory approval and for increasing the safety of enzyme products and for their use in downstream enzymatic conversions, the manufacturing and processing of enzyme products from production hosts and/or fermentation broth requires a number of individual steps to achieve compliance with the respective regulatory requirements. In industrial enzyme production it is desired to avoid expensive purification steps like chromatography for instance. Ideally, crude enzyme preparations can be used. When expressing an enzyme intracellularly an efficient and low-cost downstream processing is needed that allows producing an enzyme product that is free of recombinant DNA. The processes of the prior art, however, are not satisfactory in every respect and in consideration of the growing obligations and pre-requisites from regulatory bodies to be complied with, there is a demand for efficient and compliant manufacturing and processing processes of enzyme products.

It is an objective of the present invention to provide improved manufacturing and processing processes of enzyme products.

This problem has been solved by the subject-matter of the patent claims, sequence files and figures.

BRIEF DESCRIPTION OF THE FIGURE

FIG. 1 shows a scheme of the process for manufacturing of enzyme products.

SUMMARY OF THE INVENTION

SEQ ID NO:1 is the amino acid sequence of the nuclease from *Serratia marcescens*. SEQ ID NO:2 is the amino acid sequence of the nuclease from *Serratia marcescens* with one additional methionine at its N-terminus. SEQ ID NO: 3 is sucrose synthase 1 from *Arabidopsis thaliana* (NCBI Reference Sequence: NP_197583.1), SEQ ID NO: 4 is UDP-glycosyltransferase 76G1 from *Stevia rebaudiana* (Genbank accession no. AAR06912.1), and SEQ ID NO: 4 is beta-D-glycosyl crovetin beta-1,6-glycosyltransferase-like enzyme from *Solanum lycopersicum* (Genbank accession no. XP_004250485.1).

It could be shown that several process designs are not suitable to reduce the recombinant DNA content in a sufficient way to meet the cost efficiency and the regulatory requirements. Surprisingly it has been shown that only the combination of the following three process steps led to the desired reduction of recombinant DNA:
1. treatment with a nuclease (i.e. a nuclease enzyme) to hydrolyze DNA;
2. use of a precipitation agent and/or flocculant to precipitate hydrolyzed DNA through the formation of insoluble complexes; and
3. conduction of a subsequent microfiltration step.

Optionally, the insoluble complexes formed in step 2. may be removed by liquid/solid separation technologies prior to step 3.

Work-up of host cells that have been used in order to express recombinant enzymes typically involves various steps wherein processing additives, e.g. salts, chemical additives, enzymes or other processing aids, are added to the cultivation medium or fermentation broth, the fermentation broth may be diluted or concentrated, or physically or mechanically treated, e.g. by sonication. It has now been surprisingly found that several of such conventionally added processing additives and treatments may inhibit nucleases such that the desired hydrolysis of DNA (and/or RNA) under enzymatic catalysis of these nucleases due to the presence of these additives and process conditions may be suppressed or at least significantly inhibited. Thus, it has been surprisingly found that when utilizing such nucleases at a comparatively early step of the overall work-up procedure before such conventional processing additives are employed, desirable enzymatic hydrolysis of DNA (and/or RNA) by nucleases may be significantly improved.

Furthermore, it has been surprisingly found that the overall work-up procedure may be further improved when combining such early use of nucleases with precipitating agents (e.g. flocculants) facilitating removal of the thus hydrolyzed fragments of DNA (and/or RNA).

In a first aspect, the invention relates to a process to manufacture an enzyme product, preferably a food grade enzyme product.

Preferably, the process for the manufacture of a recombinant enzyme formulation according to the invention comprises the steps of
(i) providing a composition I comprising a recombinant enzyme, nucleic acids, and optionally cell debris;
(ii) adding to the composition I a nuclease in order to break down the nucleic acids thereby providing a composition II comprising the enzyme, broken down nucleic acids, and optionally the cell debris;
(iii) adding to the composition II a precipitation agent for the broken down nucleic acids in order to complex the broken down nucleic acids thereby providing a composition III comprising the enzyme, complexed broken down nucleic acids, and optionally the cell debris;
(iv) optionally, purifying the composition III by solid/liquid separation thereby providing a separated solid phase comprising the complexed broken down nucleic acids and optionally the cell debris and a liquid composition IV comprising the enzyme; and
(v) purifying the composition III or the composition IV by microfiltration thereby providing a composition V comprising the enzyme.

The presence of cell debris in composition I that is provided in step (i) is optional. The composition I provided in step (i) may contain disrupted cells of the microbial host to which the nuclease is added in subsequent step (ii). Alternatively, the composition I provided in step (i) may contain intact cells of the microbial host to which the nuclease is added in subsequent step (ii). Disruption of the cells of the microbial host is then preferably performed in the presence of the nuclease, e.g. by sonication.

Step (iv) is optional. Thus, the process according to the invention comprises at least steps (i), (ii), (iii) and (v); preferably (i), (ii), (iii), (iv), and (v).

The process may be performed batch-wise or continuously. While it is principally possible that a subsequent step commences before the preceding step has been terminated, the individual steps (i), (ii), (iii), (iv) and (v) are preferably performed consecutively in numerical order, wherein a subsequent step commences after the preceding step has been completely terminated. It is also contemplated, however, that additional intermediate steps which are not mentioned among steps (i), (ii), (iii), (iv) and (v) are performed in between any of steps (i), (ii), (iii), (iv) and/or (v). Additional intermediate steps may e.g. involve any physical or chemical treatment of the compositions, e.g. adjustments of temperature, pH values, or dilution or concentrations of the composition of changing of buffer compositions of the composition. Thus, nuclease treatment in step (ii) is preferably performed after step (i), and prior to any of the steps (iii), (iv) and (v).

Preferably, the nuclease is selected from the group consisting of endonucleases, exonucleases, or mixed exo/endonucleases. Preferably, the nuclease can hydrolyze DNA, RNA, or both. Preferably, the nuclease is selected from the nucleases with EC numbers attributed by the International Union of Biochemistry and Molecular Biology EC 3.1.11.2, EC 3.1.11.5, EC 3.1.11.6, EC 3.1.13.4, EC 3.1.14.1, EC 3.1.21.1, EC 3.1.21.2, EC 3.1.21.3, EC 3.1.21.4, EC 3.1.21.6, EC 3.1.25.1, EC 3.1.26.3, EC 3.1.26.4, EC 3.1.26.5, EC 3.1.26.8, EC 3.1.26.9, EC 3.1.26.11, EC 3.1.27.1, EC 3.1.27.3, EC 3.1.27.5, EC 3.1.30.1, EC 3.1.30.2, EC 3.1.31.1, and preferably EC 3.1.30.2.

Preferably, the nuclease is at least 70%, at least 75%, at least 80%, at least 85%, at least 90%, at least 95%, at least 98%, or at least 99%, identical to the sequence of SEQ ID NO:1 or SEQ ID NO:2.

Preferably, in step (ii) the nuclease is added in an amount of from 50 U to 2000 U, from 50 U to 1000 U, from 50 U to 500 U, from 100 U to 300 U, from 150 U to 300 U, and preferably of from 200 U to 300 U per gram biomass equivalent of composition II.

Preferably, the recombinant enzyme
  is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases; and/or
  is selected from the group consisting of (b-1) carbohydrate-modifying enzymes, such as glycosyl hydrolases, glycosyltransferases, polysaccharide lyases, carbohydrate esterases; (b-2) amino acid, peptide or protein-modifying enzymes, such as aminotransferases, proteases and peptidases; and (b-3) lipid modifying enzymes such as lipases or phospholipases; and/or
  a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

Preferably, the recombinant enzyme is an improved variant derived from a wild-type enzyme by known enzyme engineering technologies.

Preferably, the microfiltration in step (v) involves the removal of residual solids and/or components having a higher molecular weight than the enzyme.

Preferably, the microfiltration in step (v) involves
a) a membrane having a size exclusion limit of
  more than 1000 kDa, more than 500 kDa, more than 400 kDa, more than 300 kDa, more than 200 kDa, more than 150 kDa, more than 100 kDa, more than 90 kDa, more than 80 kDa, more than 70 kDa, more than 60 kDa, more than 50 kDa, more than 40 kDa, more than 30 kDa, or more than 20 kDa; and/or
  more than 5 µm, more than 4 µm, more than 3 µm, more than 2 µm, more than 1 µm, more than 0.5 µm, more than 0.4 µm, more than 0.3 µm, more than 0.2 µm, or more than 0.1 µm; or
b) or a filter, preferably a depth-filter with equivalent molecular weight exclusion properties,
wherein in each case the composition V is a filtrate of the microfiltration.

Preferably, the process according to the invention comprises the additional step of
(vi) purifying the composition V by an additional microfiltration or an ultrafiltration thereby providing a composition VI comprising the enzyme.

Preferably, the additional microfiltration or ultrafiltration in step (vi) involves
a) a membrane having a size exclusion limit of more than 100 kDa, more than 80 kDa, more than 60 kDa, more than 50 kDa, more than 40 kDa, more than 30 kDa, more than 20 kDa, more than 15 kDa, more than 10 kDa, more than 5 kDa, or more than 1 kDa; or
b) a filter, preferably a depth-filter, with equivalent molecular weight exclusion properties;
and wherein the composition VI is a filtrate of the microfiltration or retentate of the ultrafiltration.

Preferably, besides step (ii), the process according to the invention does not involve any additional treatment with a nuclease enzyme. Preferably, besides step (ii), the process according to the invention does not involve after the microfiltration of step (v) a treatment of the filtrate (composition VI) with a nuclease enzyme, and/or does not involve after the microfiltration of step (vi) a treatment of the filtrate (composition VI) with a nuclease enzyme, and/or does not involve after the ultrafiltration of step (vi) a treatment of the retentate (composition VI), respectively, with a nuclease enzyme.

Preferably, the process according to the invention does not involve after the liquid/solid separation step, the microfiltration step, and/or after the ultrafiltration step, respectively, a treatment of the cleared lysate, the filtrate or the retentate, respectively, with a nuclease enzyme.

Preferably, the precipitation agent is or comprises a cationic polymer, preferably selected from the group consisting of chitosan; polyamines such as polyallylamine (e.g. polydiallyldimethylammonium chloride (pDADMAC)), polyvinylamine, polyethylenimine, or poly-N-methylvinylamine (PMVA); polyamino acids such as polyarginine or polylysine; and polyacrylamides.

Preferably the precipitation agent is or comprises selected from the group consisting of polyethylenimines and polydiallyldimethyl ammonium chloride (pDADMAC).

Preferably, the precipitating agent is or comprises a flocculant. Preferred flocculants include but are not limited to
a. cationic polyamine-based flocculants, including dimethylamine-epichlorohydrin copolymer (CAS Reg No. 25988-97-0), methylamine-epichlorohydrin copolymer (CAS Reg No. 31568-35-1), dimethylamine-epichlorohydrin-ethylenediamine terpolymer (CAS Reg No. 42751-79-1); and
b. cationic polyacrylamide-based flocculants, including polyacrylamide modified by condensation with formaldehyde and dimethylamine (CAS Reg No. 67953-80-4), acrylamide-acryloxyethyl-trimethyl-ammonium chloride copolymer (CAS Reg No. 69418-26-4); and
c. anionic polyamine based flocculants, including acrylamide-acrylic acid copolymer (CAS Reg No. 25987-30-8; CAS Reg No. 9003-06-9); and
d. ammonium sulfate (CAS Reg No. 10043-01-3); and
e. calcium chloride (CAS Reg No. 10035-04-8; CAS Reg No. 10043-52-4).

Preferably, composition V obtained in step (v) and/or composition VI obtained in optional step (vi) is characterized by a residual DNA concentration of from 0 ng/g to 50 ng/g, of from 0 ng/g to 40 ng/g, of from 0 ng/g to 30 ng/g, of from 0 ng/g to 20 ng/g, of from 0 ng/g to 10 ng/g, of from 0 ng/g to 9 ng/g, of from 0 ng/g to 8 ng/g, of from 0 ng/g to 7 ng/g, of from 0 ng/g to 6 ng/g, of from 0 ng/g to 5 ng/g, of from 0 ng/g to 4 ng/g, of from 0 ng/g to 3 ng/g, of from 0 ng/g to 2 ng/g, of from 0 ng/g to 1 ng/g, and preferably of from 0 ng/g to 0.9 ng/g, of from 0 ng/g to 0.8 ng/g, of from 0 ng/g to 0.7 ng/g, of from 0 ng/g to 0.6 ng/g, of from 0 ng/g to 0.5 ng/g, of from 0 ng/g to 0.4 ng/g, of from 0 ng/g to 0.3 ng/g, of from 0 ng/g to 0.2 ng/g, and of from 0 ng/g to 0.1 ng/g, or more preferably of below 0.1 ng/g, and most preferably of below 0.01 ng/g.

Preferably, step (i) involves one or more of the following sub-steps:
(i-a) cloning of a gene for the enzyme into an expression vector;
(i-b) introducing the expression vector carrying the gene into a microbial host;
(i-c) intracellularly expressing the enzyme in a microbial host; i.e. fermenting the microbial host under conditions of intracellular expression of the recombinant enzyme; and
(i-d) releasing the enzyme (and the nucleic acids) from the microbial host by cell disruption thereby providing the composition I; i.e. disrupting the fermented cells by cell disruption for releasing of the recombinant enzyme resulting in a crude lysate comprising recombinant enzyme product.

Thus, according to this preferred embodiment, the cells of the microbial host are disrupted in step (i), substep (i-d) and the nuclease is added in subsequent step (ii).

However, it is alternatively also contemplated that the cells of the microbial host are suspended e.g. in cell lysis buffer containing the nuclease and then disrupted e.g. by sonication in the presence of the nuclease already. Thus, according to this embodiment, step (ii) preferably involves the following substeps:
(ii-a) adding to the composition I a nuclease;
(ii-b) releasing the recombinant enzyme and the nucleic acids from the microbial host by cell disruption in order to break down the nucleic acids thereby providing a composition II comprising the recombinant enzyme, broken down nucleic acids, and the cell debris; i.e. disrupting the fermented cells by cell disruption for releasing of the recombinant enzyme and the nucleic acids resulting in a crude lysate comprising recombinant enzyme, broken down nucleic acids, and cell debris (and nuclease).

Preferably, the microbial host
is *Escherichia coli*, preferably a genetically modified derivative strain of the laboratory strain *E. coli* K-12 W3110, and most preferably LE1B109; and/or
is modified by deletion of one or more additional genes selected from the group consisting of the genes encoding the enzymes, preferably the *E. coli* enzymes, phosphoglucomutase, alkaline phosphatase, glucose-1-phosphate phosphatase, UDP-glucose 6-dehydrogenase, cellulose synthase (UDP-forming), alpha,alpha-trehalose-phosphate synthase (UDP-forming), UDP-glucose-hexose-1-phosphate uridylyltransferase, UTP-glucose-1-phosphate uridylyltransferase, UTP-glucose-1-phosphate uridylyltransferase, UDP-sugar diphosphatase, nucleotide diphosphatase, UDP-glucose 4-epimerase, ribonucleoside-diphosphate reductase, ribonucleoside-diphosphate reductase, lipopolysaccharide N-acetylmannosaminouronosyltransferase, lipid-A-disaccharide synthase, undecaprenyldiphospho-muramoylpentapeptide beta-N-acetylglucosaminyltransferase, undecaprenyl-phosphate 4-deoxy-4-formamido-L-arabinose transferase, 6-phosphofructokinase, pyruvate kinase, uridine kinase, UMP kinase, nucleoside-diphosphate kinase, polyribonucleotide nucleotidyltransferase, UDP-N-acetylglucosamine 2-epimerase (non-hydrolyzing), beta-galactosidase, N-acetylneuraminate lyase, N-acetylmannosamine kinase, putative N-acetylmannosamine-6-phosphate 2-epimerase, alpha-galactosidase, galactoside O-acetyltransferase.

Preferably, e.g. in a first embodiment of the first aspect of the invention, or clause 1, the invention relates to a process to manufacture a food-grade enzyme product that comprises the following steps:
a. intracellular expression of a recombinant enzyme in a microbial host
b. release of the recombinant enzyme by cell disruption resulting in a crude lysate,
c. addition of a nuclease to break down nucleic acids in the enzyme product containing process solution resulting in an enzyme-treated lysate;
d. addition of a precipitation agent to complex nucleic acids resulting in a complexed lysate;
e. liquid/solid separation to remove cell debris and nucleic acid/precipitation agent complexes from the liquid phase resulting in a cleared lysate; and
f. conducting a microfiltration step to remove residual solids, and/or high molecular weight components, resulting in a filtrate;
wherein the process does preferably not involve after the liquid/solid separation of step e. a treatment of the cleared lysate, or after the microfiltration step f. a treatment of the filtrate, respectively, with a nuclease enzyme.

The process may be performed batch-wise or continuously. While it is principally possible that a subsequent step commences before the preceding step has been terminated, the individual steps a.), b.), c.), d.), e.) and f.) are preferably performed consecutively in alphabetical order, wherein a subsequent step commences after the preceding step has been completely terminated. It is also contemplated, however, that additional intermediate steps which are not mentioned among steps a.), b.), c.), d.), e.) and f.) are performed in between any of steps a.), b.), c.), d.), e.) and/or f.).

Preferably, in a preferred embodiment of the first aspect of the invention, the invention relates to a process for the manufacture of a recombinant enzyme formulation, said process comprising the steps of providing a composition I comprising a recombinant enzyme product, nucleic acids, and optionally cell debris;
(ii) adding to the composition I a nuclease in order to break down the nucleic acids thereby providing a composition II comprising the enzyme product, broken down nucleic acids, and optionally the cell debris;
(iii) adding to the composition II a precipitation agent for the broken down nucleic acids in order to complex the broken down nucleic acids thereby providing a composition III comprising the enzyme product, complexed broken down nucleic acids, and optionally the cell debris;
(iv) optionally, purifying the composition III by solid/liquid separation thereby providing a separated solid phase comprising the complexed broken down nucleic acids and optionally the cell debris and a liquid composition IV comprising the enzyme product; and
(v) purifying the composition III or the composition IV by microfiltration thereby providing a composition V comprising the enzyme product;
wherein the process preferably does not involve after the liquid/solid separation of step (iv) a treatment of the cleared lysate (composition IV) with a nuclease enzyme, or after the microfiltration step (v) a treatment of the filtrate (composition V), respectively, with a nuclease enzyme.

Preferably, in a preferred embodiment of the firsts aspect of the invention, the invention relates to a process for the manufacture of a recombinant enzyme formulation, said process comprising the steps of
(i) providing a composition I comprising a recombinant enzyme product, nucleic acids, and optionally cell debris;
(ii) adding to the composition I a nuclease in order to break down the nucleic acids thereby providing a composition II comprising the enzyme product, broken down nucleic acids, and optionally the cell debris;
(iii) adding to the composition II a precipitation agent for the broken down nucleic acids in order to complex the broken down nucleic acids thereby providing a composition III comprising the enzyme product, complexed broken down nucleic acids, and optionally the cell debris;
(iv) optionally, purifying the composition III by solid/liquid separation thereby providing a separated solid phase comprising primarily complexed broken down nucleic acids, and optionally the cell debris, and optionally remainders of the enzyme product derived from composition III, and a liquid composition IV comprises primarily the enzyme product, and optionally remainders of cell debris and complexed broken down nucleic acids derived from composition III; and
(v) purifying the composition III or the composition IV by microfiltration thereby providing a composition V comprising the enzyme product;
wherein the process preferably does not involve after the liquid/solid separation of step (iv) a treatment of the cleared lysate (composition IV) with a nuclease enzyme, or after the microfiltration step (v) a treatment of the filtrate (composition V), respectively, with a nuclease enzyme.

In a preferred embodiment, preferably of the first aspect of the invention, or any of the embodiments of the first aspect, the invention relates to a process for the manufacture of a recombinant enzyme product, which comprises after step (v) an additional step (vi) of purifying the composition V by an additional microfiltration or an ultrafiltration, thereby providing a composition VI comprising the enzyme product.

It is within the scope of this invention, that after the microfiltration of step (v) and/or after the microfiltration of step (vi), a filtrate (composition V or composition VI) is obtained, which contains the enzyme product. It is also within the scope of this invention, that after the ultrafiltration of step (vi), a retentate (composition VI) is obtained, which contains the enzyme product.

Preferably the process does not involve after the microfiltration of step (v) a treatment of the filtrate (composition VI) with a nuclease enzyme, and/or does not involve after the microfiltration of step (vi) a treatment of the filtrate (composition VI) with a nuclease enzyme, and/or does not involve after the ultrafiltration of step (vi) a treatment of the retentate (composition VI), respectively, with a nuclease enzyme.

In a preferred embodiment, preferably of the first aspect of the invention, or any of the embodiments of the first aspect, the invention relates to a process for the manufacture of a recombinant enzyme product, wherein the enzyme product can be distinguished from other preparations by the absence of DNA fragments in the preparation of the enzyme product.

It is within the scope of the invention that the terms composition I and crude lysate, the terms composition II and enzyme-treated lysate, the terms composition III and complexed lysate, and the terms composition IV and cleared lysate, respectively, are considered to be equivalent and are used in an equivalent way, and describe the same element of the invention.

It is in the scope of this invention, that the terms "enzyme product" and "recombinant enzyme formulation" are considered to be equivalent and are used in an equivalent way, and describe the same element of the invention.

It is further within the scope of the invention that the enzyme product of the invention is comprised in liquid compositions I, II, III, IV, V, and IV, and preferably the enzyme product of the invention is the liquid composition V, composition VI, or any other liquid, lyophilized, or stabilized formulation derived therefrom.

Preferably, e.g. in a second embodiment of the first aspect of the invention, or clause 2, which is also an embodiment of the first embodiment and any other embodiments of the first aspect, the invention relates to a process for the manufacture of a recombinant enzyme product, which is characterized that comprises one or more of the following steps:
a. cloning of an enzyme product gene into an expression vector;
b. introducing the expression vector carrying the enzyme product gene into a microbial host;
c. fermentation of the microbial host of step (b) above under conditions of intracellular expression of the recombinant enzyme product;
d. disrupting the fermented cells of step (c) above by cell disruption for release of the recombinant enzyme product resulting in a crude lysate containing recombinant enzyme product;
e. incubation of the crude lysate with a nuclease in order to break down nucleic acids from the crude lysate resulting in an enzyme-treated lysate;
f. addition of a precipitation agent to the enzyme-treated lysate for the formation of complexes of nucleic acids resulting in a complexed lysate containing recombinant enzyme product;
g. liquid and/or solid separation of the complexed lysate to remove cell debris and complexes of nucleic acid and precipitation agent from the liquid phase, resulting in a cleared lysate containing recombinant enzyme product; and
h. submission of the enzyme-treated, and optionally cleared lysate to a microfiltration step to remove residual solids and/or high molecular weight components;
wherein the process preferably does not involve after the liquid/solid separation of step g. a treatment of the cleared lysate, or after the microfiltration step h. a treatment of the filtrate, respectively, with a nuclease enzyme.

The process may be performed batch-wise or continuously. While it is principally possible that a subsequent step commences before the preceding step has been terminated, the individual steps a.), b.), c.), d.), e.), f.), g.) and h.) are preferably performed consecutively in alphabetical order, wherein a subsequent step commences after the preceding step has been completely terminated. It is also contemplated, however, that additional intermediate steps which are not mentioned among steps a.), b.), c.), d.), e.), f.), g.) and h.) are performed in between any of steps a.), b.), c.), d.), e.), f.), g.) and/or h.).

In a preferred embodiment, preferably of the first aspect of the invention, which is also an embodiment of any other embodiments of the first aspect, the invention relates to a process for the manufacture of a recombinant enzyme product, wherein the solid/liquid separation of step (iv), step (e) (for clause 1), or step (g) (for cause 2), is omitted.

It is within the disclosure of the first, the second, and any other embodiment of the first aspect of the invention, that the process may comprise one or more of the steps thereof. It is also within the disclosure of the first, the second, and any other embodiment of the first aspect of the invention, that the process comprises each of the steps thereof. It is also within the disclosure the first and any other embodiment of the first aspect of the invention, that the step of nuclease treatment in step (c), or (ii), is mandatory to happen after any of the steps (a, b), or (i), and prior to any of the steps (d, e, f), or (iii, iv, v). It is also within the disclosure the second embodiment of the first aspect of the invention, that the step of nuclease treatment in step (e) is mandatory to happen after any of the steps (a, b, c, d) and prior to any of the steps (f, g, h).

In a preferred embodiment, preferably of the first aspect of the invention, which is also an embodiment of any other embodiments to the first aspect, the present invention does not involve after the liquid/solid separation, and after the microfiltration step, and after the ultrafiltration step, respectively, a treatment of the cleared lysate, the filtrate or the retentate, respectively, with a nuclease enzyme. Preferably, the step (c), or (ii) of the first embodiment of the first aspect is realized after step (f), or (v) of the first embodiment of the first aspect of the invention, and that preferably the step (e) of the second embodiment of the first aspect is realized after step (h) of the second embodiment of the first aspect.

For the purpose of the invention, the crude lysate obtained in step (b) for clause 1, or (i), of the first embodiment, or in step (d) for clause 2 of the second embodiment of the first aspect of the invention, is an enzyme product, which is a recombinant crude enzyme preparation of intracellularly expressed enzymes and is defined as an enzyme preparation that is obtained after cell disruption of a microorganism that expresses a recombinant enzyme as intracellular protein. The crude lysate may contain besides the recombinant enzyme product, for example, lipids, metabolites, carbohydrates, membrane fragments, derivatives from any of those biomolecules, and/or intracellular host cell proteins which can be detected for instance by host-specific immune assays. Corresponding antibodies which are directed against host cell proteins, for instance from *Escherichia coli*, are available from different sources. A Western Blot can be applied. The purity of the recombinant crude enzyme preparation on the protein level which for instance can be determined by SDS-PAGE based methods is ≤50%, preferred ≤60%, more preferred ≤70%, even more preferred ≤80% and most preferred ≤90%.

For the purpose of the invention, the fermentation conditions are a pH of between 6 to 8 and a temperature of between 25° C. to 37° C. The fermentation process is continued until laboratory test data show the desired enzyme production yield. Then, usually after at least 15 hours, the fermentation is stopped. In a subsequent recovery process, the enzyme is isolated from the biomass. In a first solid/liquid separation, the biomass is separated from the culture broth by standard techniques (e.g., is centrifuged and/or filtered). The biomass is homogenized to disrupt the bacterial cells and treated with a nuclease to degrade the DNA/RNA nucleic acids released upon cell disruption. This is followed by solid/liquid separation steps to further remove cell debris and other insoluble matter. The cell-free supernatant is filtered to obtain the purified enzyme preparation. All raw materials used for fermentation and recovery are of food-grade quality or have been assessed to be fit for their intended use. The enzyme products obtained may then be subjected to a downstream enzymatic conversion. FIG. 1 shows a scheme of the manufacturing of enzyme products described hereunder.

Preferably, e.g. in a third embodiment of the first aspect of the invention, which is also an embodiment of the first and the second and any other embodiment of the first aspect of the invention, the invention relates to a process, wherein the microbial host is *Escherichia coli*, preferably a genetically modified derivative strain of the laboratory strain *E. coli* K-12 W3110, and most preferably is LE1B109.

Preferably, the invention also relates to a process, wherein a recombinant enzyme
- selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases; and/or
- selected from the group consisting of (b-1) carbohydrate-modifying enzymes, such as glycosyl hydrolases, glycosyltransferases, polysaccharide lyases, carbohydrate esterases; (b-2) amino acid, peptide or protein-modifying enzymes, such as aminotransferases, proteases and peptidases; and (b-3) lipid modifying enzymes such as lipases or phospholipases; and/or
- which is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase;

has been expressed in the microbial host *Escherichia coli*, preferably in a genetically modified derivative strain of the laboratory strain *E. coli* K-12 W3110, and most preferably in LE1B109.

Preferably, the recombinant enzyme that has been expressed in the microbial host *Escherichia coli*, preferably in a genetically modified derivative strain of the laboratory strain *E. coli* K-12 W3110, and most preferably in LE1B109, is a known wild-type enzyme or any improved variant derived therefrom by known enzyme engineering technologies.

It is within the disclosure of the third embodiment of the first aspect of the invention, that the production strain LE1B109 is a genetically modified derivative strain of the laboratory strain *E. coli* K-12 W3110.

The K-12 strain, and in particular the W3110 sub strain, has been safely used as a laboratory organism for more than 50 years and is one of the most extensively characterized bacteria (Bachmann, 1972; Jensen, 1993).

*E. coli* K-12 has a long history of safe use in the industrial production of specialty chemicals and human drugs (U.S. EPA, 1997). For example, a food enzyme preparation (chymosin) obtained from a genetically modified *E. coli* K-12 strain was affirmed as GRAS by the U.S. FDA in 1990 (Flamm, 1991; Olempska-Beer et al., 2006) and has been used safely for cheese production worldwide. In the European Union there are currently 3 food enzyme preparations derived from *E. coli* K-12 being assessed by EFSA as part of the requirements for authorization in accordance with Regulation (EC) 1331/2008 (European Commission, 2016). One of them, D-allulose 3-epimerase, has recently been the subject of a GRAS notification, receiving no questions from the U.S. FDA (U.S. FDA, 2016). The other two food enzyme preparations derived from *E. coli* K-12, two different cyclomaltodextrin glucotransferases, have been safely used for years in the production of the novel food ingredients alpha- and gamma-cyclodextrin, authorized by the European Commission in 2008 and 2012, respectively.

*E. coli* K-12 is not considered a human or animal pathogen and has accordingly been classified as belonging to Risk Group 1 in the NIH Guidelines (NIH, 2016). Moreover, it is often used as a non-pathogenic reference when studying the virulence factors of pathogenic *E. coli* strains (Blanc-Potard et al., 2002; Kaper et al., 2004). *E. coli* K-12 and its derivatives are essentially unable to colonize the mammalian gastrointestinal tract, do not produce toxins that cause illness upon ingestion, including Shiga toxin, and are unable to persist in either water or soil (Bogosian et al., 1996; U.S. EPA, 1997). The parental laboratory strain W3110 does not carry any introduced antimicrobial resistance genes. The complete genomes of *E. coli* K-12 and specifically of the sub-strain W3110 have been sequenced, confirming the absence of toxigenic potential (Blattner et al., 1997; Hayashi et al., 2006).

The parental strain *E. coli* K-12 W3110 belongs to the well-defined taxonomic family of the Enterobacteriaceae. The primary habitat of *E. coli* is the lower intestinal tract of warm-blooded animals, where it represents the predominant aerobic microorganism. Non-pathogenic strains of *E. coli* are considered as commensal, although the host also derives some beneficial effects, mainly by preventing colonization by pathogens (Tenaillon et al., 2010).

It is within the scope of the present invention for creation of the production strain LE1B109 the parental strain *E. coli* K-12 W3110 has been modified by site-directed recombination at different chromosomal loci to suit production purposes in terms of genetic stability, especially plasmid stability, and efficiency of expression and downstream enzymatic conversions. The expression of a number of proteases has been eliminated by deletion of the corresponding genes. Antibiotic-free selection of target clones has been enabled through deletion of one gene. One further gene has been deleted to prevent unwanted recombination effects. The gene coding for the T7 RNA polymerase from *E. coli* T7 phage and another gene copy of lacI, a repressor naturally present in *E. coli* K-12 W3110, have been inserted into the genome of W3110 to achieve a strong and regulated enzyme expression.

Preferably, it is within the scope of the invention that the enzyme production strain *E. coli* LE1B109 is a derivative of the parental strain *E. coli* K-12 W3110. Prior to use, its genome has been analyzed and absence of antibiotic resistance genes or any other sequence of concern has been confirmed to meet food enzyme legislation requirements. The enzyme production strain was evaluated using the decision tree developed by Pariza and Johnson (2001), and was accepted based on the conclusion that the final products of an enzymatic conversion meet JECFA specifications. The absence of the production microorganism in the final enzyme product preparations is demonstrated for each enzyme batch, according to the product specifications, to be in compliance with food quality requirements.

It is furthermore within the scope of the invention, that the production strain may carry certain deletions of endogenous enzyme genes connected to the degradation of certain reactants or intermediates in a downstream enzyme conversion, in order to avoid side reactions. Deletions of chromosomal DNA is in general performed by removal of target genes by homologous recombination technologies, for example by integration of plasmid-based fragments carrying antibiotic resistance genes or other selection markers. Similarly, if required, insertions of new genes can be obtained. After selection of the correct chromosomal mutants, resistance genes are excised by transiently expressed enzymes. Alternatively, cells that have lost unwanted sequences (for example, plasmid encoded genes or entire plasmids) can be selected by negative selection pressure, e.g. expression of suicide markers. No residual vector sequences or antibiotic resistance genes are left in the final cell, in compliance with food enzyme requirements.

It is within the disclosure of the third embodiment of the first aspect that within the manufacturing process for enzyme products, the *E. coli* production strain LE1B109 carrying the expression vector for the corresponding enzyme of interest is inoculated in sterilized culture medium composed of glucose and defined mineral components as fermentation nutrient and fermented.

Preferably, e.g. in a fourth embodiment of the first aspect of the invention, which is also an embodiment of the first and the second and the third and any other embodiment of the first aspect of the invention, the invention relates to a process, wherein the expression vector is based on the well-known vector pRSF-1b (Novagen). For the purpose of the invention, the genes for enzyme products are cloned into the expression vector and the expression of the gene is induced during fermentation by supplementing Isopropyl β-D-1-thiogalactopyranoside (IPTG) as inducer for enzyme expression.

It is within the disclosure of the fourth embodiment and any other embodiment of the first aspect of the invention that the final production strain used for manufacturing of a specific enzyme is created from the LE1B109 recipient strain by introducing an expression vector carrying the specific gene of the desired enzymes. The plasmids used to transform the *E. coli* recipient strain are based on the well-known vector pRSF-1b. The plasmids have been fully sequenced and do not carry antibiotic resistance genes or any other sequences of concern. Thereafter the production strain LE1B109 is sequenced to confirm absence of antibiotic resistance genes or any other sequences of concern.

In a preferred embodiment, preferably of the first aspect of the invention, which is also an embodiment of any other embodiments thereof, the final production strain used for manufacturing of a specific enzyme is created from the LE1B109 recipient strain by integrating the specific gene of the desired enzymes into the genome of LE1B109 by use of suitable integration vectors or DNA fragments based on homologous recombination technologies.

Preferably, e.g. in a fifth embodiment of the first aspect of the invention, which is also an embodiment of the first and the second and the third and the fourth and any other embodiment of the invention, the invention relates to a process, wherein the expression vector does not carry antibiotic resistance genes or any other sequences of concern.

Preferably, e.g. in a sixth embodiment of the first aspect of the invention, which is also an embodiment of the first and the second and the third and the fourth and the fifth and any other embodiment of the first aspect, the invention relates to a process, wherein a suitable antifoam agent is added in step (a) of the first embodiment (clause 1) of the first aspect or in step (c) of the second embodiment (clause 2) of the first aspect. For the purpose of the invention, such antifoam agents are chosen which comply with specific quality requirements for manufacturing of an enzyme product. Specifically, it is within the disclosure of the invention, that antifoam agents are listed in the U.S. FDA Sep. 11, 2003 letter to FTA as being acceptable for use in manufacturing of enzyme products. For the purpose of this invention, antifoam agent may be selected from the group consisting of the antifoam agents polypropylene glycol (CAS Reg No. 25322-69-4), polyglycerolpolyethylene-polypropylene block copolymer (CAS Reg No. 78041-14-2), polyoxyethylene-polyoxypropylene block copolymer (CAS Reg No. 9003-11-6), polypropylene glycerol monobutyl ether (CAS Reg No. 9003-13-8), polydimethylsiloxane (CAS Reg No. 63148-62-9; CAS Reg No. 68083-18-1), silica (CAS Reg No. 7631-86-9; CAS Reg No. 63231-67-4), stearic acid (CAS Reg No. 57-11-4), sorbitan sesquioleate (CAS Reg No. 8007-43-0), glycerol monostearate (CAS Reg No. 123-94-4), polysorbates (polyoxyethylene sorbitan fatty acid esters like polysorbate 60 (CAS Reg No. 9005-67-8), polysorbate 65 (CAS Reg No. 9005-71-4), and polysorbate 80 (CAS Reg No. 9005-65-6), rape oil mono- and diglycerides (CAS Reg No. 93763-31-6), and white mineral oil (CAS Reg No. 64742-47-8).

According to the invention, preferred precipitating agents are flocculants. Preferably, e.g. in a seventh embodiment of the first aspect of the invention, which is also an embodiment of the first and the second and the third and the fourth and the fifth and the sixth and any other embodiment of the first aspect, the invention relates to a process, wherein one or more suitable flocculants is/are added, preferably in step (a) or in step (d) of the first embodiment of the first aspect (clause 1), or preferably in step (c) or step (f) of the second embodiment of the first aspect (clause 2). For the purpose of the invention, such flocculants are chosen which comply with specific quality requirements for manufacturing of an enzyme product. Specifically, it is within the disclosure of the invention, that flocculants are listed in the U.S. FDA Sep. 11, 2003 letter to FTA as being acceptable for use in manufacturing of enzyme products.

For the purpose of this invention, flocculants are selected from the group consisting of the flocculants of
a. cationic polyamine-based flocculants, including dimethylamine-epichlorohydrin copolymer (CAS Reg No. 25988-97-0), methylamine-epichlorohydrin copolymer (CAS Reg No. 31568-35-1), dimethylamine-epichlorohydrin-ethylenediamine terpolymer (CAS Reg No. 42751-79-1); and b. cationic polyacrylamide-based flocculants, including polyacrylamide modified by condensation with formaldehyde and dimethylamine (CAS Reg No. 67953-80-4), acrylamide-acryloxyethyl-trimethyl-ammonium chloride copolymer (CAS Reg No. 69418-26-4); and c. anionic polyamine based flocculants, including acrylamide-acrylic acid copolymer (CAS Reg No. 25987-30-8; CAS Reg No. 9003-06-9); and d. ammonium sulfate (CAS Reg No. 10043-01-3); and e. calcium chloride (CAS Reg No. 10035-04-8; CAS Reg No. 10043-52-4).

Preferably, e.g. in an eight embodiment of the first aspect of the invention, which is also an embodiment of the first and the second and the third and the fourth and the fifth and the sixth and the seventh and any other embodiment of the first aspect, the invention relates to a process, wherein the precipitation agent is selected from the group consisting of polyethylenimines and polydiallyldimethyl ammonium chloride.

Preferably, e.g. in a ninth embodiment of the first aspect of the invention, which is also an embodiment of the first and the second and the third and the fourth and the fifth and the sixth and the seventh and the eighth and any other embodiment of the first aspect, the invention relates to a process, wherein the precipitation agent is selected from the group consisting of the precipitation agents Superfloc® 781 G, Superfloc® C448, Superfloc® C581 G, Superfloc® C752, Superfloc® SD-2081, and polyethylenimine Lupasol®.

In a preferred embodiment, preferably of the first aspect of the invention or of any of its embodiments, the release of the enzyme from the microbial host for providing the composition I according step (b) of the first embodiment of the first aspect (clause 1) or step (d) of the first embodiment of the first aspect (clause 2), is accomplished by cell disruption technologies known in the state of the art, including and only for example, homogenization, French press, bead mills, chemical treatment, enzymatic treatment, freeze-thaw cycles or ultrasonic treatment.

It is within the scope of the invention, that the composition I obtained by homogenization may be derived directly from fermentation broth. It is also within the scope of the invention that a fermentation broth may be further processed prior to cell disruption, and in particular may be concentrated to higher cell densities (amount cells per volume) or may be diluted to lower cell densities. The resulting "concentrated cells" preparation or "diluted cells" preparation then can be subjected to cell disruption for providing composition I according to the invention.

It is within the scope of the invention, that the composition I obtained by cell disruption technologies according to the invention may constitute a cell homogenate, or any other partially or fully purified cell-free preparation derived from such cell homogenate.

Preferably, e.g. in a tenth embodiment of the first aspect of the invention, which is also an embodiment of the first and the second and the third and the fourth and the fifth and the sixth and the seventh and the eighth and the ninth and any other embodiment of the invention, the invention relates to a process wherein a nuclease is added, which nuclease is selected from the group consisting of endonucleases, exonucleases, or mixtures of endonucleases and exonucleases. Preferably, the nuclease can hydrolyze DNA, RNA, or both. Preferably, the nuclease is selected from the nucleases with EC numbers attributed by the International Union of Biochemistry and Molecular Biology EC 3.1.11.2, EC 3.1.11.5, EC 3.1.11.6, EC 3.1.13.4, EC 3.1.14.1, EC 3.1.21.1, EC 3.1.21.2, EC 3.1.21.3, EC 3.1.21.4, EC 3.1.21.6, EC 3.1.25.1, EC 3.1.26.3, EC 3.1.26.4, EC 3.1.26.5, EC 3.1.26.8, EC 3.1.26.9, EC 3.1.26.11, EC 3.1.27.1, EC 3.1.27.3, EC 3.1.27.5, EC 3.1.30.1, EC 3.1.30.2, EC 3.1.31.1, and preferably EC 3.1.30.2.

Several nuclease enzymes are known in the prior art, which can cleave DNA and/or RNA molecules either from the 3' or 5'-termini or internally, or which show both activities. For the purpose of the invention, the nuclease is able to efficiently cleave DNA/RNA prior to any microfiltration and/or ultrafiltration processing. Cleavage or break down of nucleic acids shall mean the hydrolytic cleavage of the ester bonds between the nucleotide monomers of a DNA or RNA polynucleotide, resulting in the formation of shortened polynucleotides, and/or oligonucleotides of any length down to tri-, di-, or mononucleotides sizes. It is within the scope of the invention, that a polynucleotide may comprise desoxyribonucleotides, ribonucleotides, any chemical modification of desoxyribonucleotides or ribonucleotides, or combinations of any of them.

Preferably, e.g. in a eleventh embodiment of the first aspect of the invention, which is also an embodiment of the first and the second and the third and the fourth and the fifth and the sixth and the seventh and the eighth and the ninth and the tenth and any other embodiment of the invention, the invention relates to a process wherein a nuclease is added, wherein the nuclease is at least 70% identical to the sequence of SEQ ID NO:1 or SEQ ID NO:2. The nuclease of the invention can be detected with immune assays that make use of an antibody that is directed against the nuclease of the invention. For instance a corresponding ELISA kit is commercially available from Merck.

It is within the scope of the invention that the nuclease according to the invention comprises such an amino acid sequence with a defined identity to the amino acid sequence of inventive SEQ ID NO:1 or SEQ ID NO:2. This means that the nuclease according to the invention may comprise said amino acid sequence as a subsequence of its overall amino acid sequence, or that the nuclease according to the invention may essentially consist of said amino acid sequence. When the nuclease according to the invention comprises said amino acid sequence as a subsequence of its overall amino acid sequence, said overall amino acid sequence may be extended, i.e. may comprise additional amino acid residues, at the N-terminus and/or at the C-terminus of said subsequence. Such extension may be advantageous, for example, when the nuclease is to be immobilized on a solid support, e.g. for purification purposes. Furthermore, such extension may also occur in enzyme precursor molecules of the mature nuclease enzymes of SEQ ID NO:1 and/or SEQ ID NO:2, for example naturally occurring or added signal peptide sequences or pro-peptide sequences of the enzyme. In particular, the nuclease according to the invention may be extended by the one additional amino acid methionine at the N-terminus of the amino acid sequence with at least 70% identity to SEQ ID NO:1 or SEQ ID NO:2, which methionine residue may derive from recombinant expression of the respective nuclease in microbial hosts like *E. coli* i.e. SEQ ID NO:2.

It is known how the identity and homology, respectively, of a polymer of amino acid residues is determined. For the purpose of this invention, homology and identity are understood as synonyms. Percent identity is calculated as: Sequence Identity [%]=number of Matches/L×100, wherein L is the number of aligned positions, i.e. identities and non-identities (including gaps, if any). In the meaning of this invention, the identity is preferably calculated using BLASTP (see for example Stephen F. Altschul, Thomas L. Madden, Alejandro A. Schäffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schäffer, and Yi-Kuo Yu (2005) "Protein database searches using compositionally adjusted substitution matrices." FEBS J. 272:5101-5109), preferably with the following algorithm parameters: Matrix: BLOSUM62; Gap Costs: Existence: 11 Extension: 1, Expect threshold: 10 and Word size: 6. Results are filtered for sequences with more than 35% query coverage. BlastP can be accessed online at the NCBI Homepage (blast.ncbi.nlm.nih.gov/Blast.cgi?PROGRAM=blastp&PAGE_TYPE=BlastSearch&LINK_LOC=blasthome). Other program setting can be adjusted as desired, for example using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 100 to 20000, preferably 20000; Short queries: Automatically adjust parameters for short input sequences; Expect threshold: 10; Word size: 6; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none.

Preferably, the nuclease comprises an amino acid sequence with an identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 93.1%, at least 93.2%, at least 93.3%, at least 93.4%, at least 93.5%, at least 93.6%, at least 93.7%, at least 93.8%, at least 93.9%, more preferably at least 94%, at least 94.1%, at least 94.2%, at least 94.3%, at least 94.4%, at least 94.5%, at least 94.6%, at least 94.7%, at least 94.8%, at least 94.9%, still more preferably at least 95%, at least 95.1%, at least 95.2%, at least 95.3%, at least 95.4%, at least 95.5%, at least 95.6%, at least 95.7%, at least 95.8%, at least 95.9%, yet more preferably at least 96%, at least 96.1%, at least 96.2%, at least 96.3%, at least 96.4%, at least 96.5%, at least 96.6%, at least 96.7%, at least 96.8%, at least 96.9%, even more preferably at least 97%, at least 97.1%, at least 97.2%, at least 97.3%, at least 97.4%, at least 97.5%, at least 97.6%, at least 97.7%, at least 97.8%, at least 97.9%, most preferably at least 98%, at least 98.1%, at least 98.2%, at least 98.3%, at least 98.4%, at least 98.5%, at least 98.6%, at least 98.7%, at least 98.8%, at least 98.9%, and in particular at least 99%, at least 99.1%, at least 99.2%, at least 99.3%, at least 99.4%, at least 99.5%, at least 99.6%, at least 99.7%, at least 99.8%, at least 99.9%, to the amino acid sequence of SEQ ID NO:1 or SEQ ID NO:2. In a preferred embodiment, the nuclease comprises an amino acid sequence the essentially consists of the amino acid sequence of inventive SEQ ID NO:1 or SEQ ID NO:2. In a preferred embodiment, the nuclease consists of the amino acid sequence of inventive SEQ ID NO:1 or SEQ ID NO:2.

In a preferred embodiment, the nuclease according to the invention is a fusion protein of the amino acid sequence of inventive SEQ ID NO:1 or SEQ ID NO:2 with any other amino acid, oligo- or polypeptide, which is fused to the N-terminus and/or the C-terminus. Most preferred, the nuclease according to the invention is a fusion protein with methionine, which is fused to the N-terminus.

It is within the scope of this invention, that any N-terminal or C-terminal amino acid extensions in a fusion protein of the amino acid sequence of inventive SEQ ID NO:1 or SEQ ID NO:2 are disregarded in calculating of sequence identities between the extended and a non-extended amino acid sequence, and that the fusion sequence shall not contribute to the calculation of sequence identities between the non-fused and the fusion protein using the algorithms described herein.

Preferably, e.g. in a twelfth embodiment of the first aspect of the invention, which is also an embodiment of the first and the second and the third and the fourth and the fifth and the sixth and the seventh and the eighth and the ninth and the tenth and the eleventh and oaf any other embodiment of the invention, the invention relates to a process wherein the amount of nuclease used per ml of treated preparation, including fermentation broth, cell concentrate, homogenate, or any other preparation disclosed herein, and preferably of composition II, is more than 1,000 U, more than 900 U, more than 800 U, more than 700 U, more than 600 U, more than 500 U, more than 400 U, more than 300 U, more than 200 U, more than 100 U, more than 50 U, more than 40 U, more than 30 U, more than 20 U, more than 15 U, more than 10 U, more than 5 U, more than 3 U, more than 2 U, more than 1 U, more than 0.5 U or more than 0.1 U; or from 0.1 U to 1000 U, from 0.1 U to 900 U, from 0.1 U to 800 U, from 0.1 U to 700 U, from 0.1 U to 600 U, from 0.1 U to 500 U, from 0.1 U to 400 U, from 0.1 U to 300 U, from 0.1 U to 200 U, from 0.1 U to 100 U, from 0.1 U to 90 U, from 0.1 U to 80 U, from 0.1 U to 70 U, from 0.1 U to 60 U, from 0.1 U to 50 U, from 0.1 U to 40 U, from 0.1 U to 30 U, from 0.1 U to 20 U, from 0.1 U to 19 U, from 0.1 U to 18 U, from 0.1 U to 17 U, from 0.1 U to 16 U, from 0.1 U to 15 U, from 0.1 U to 14 U, from 0.1 U to 13 U, from 0.1 U to 12 U, from 0.1 U to 11 U, from 0.1 U to 10 U, from 0.1 U to 9 U, from 0.1 U to 8 U, from 0.1 U to 7 U, from 0.1 U to 6 U, from 0.1 U to 5 U, from 0.1 U to 4 U, from 0.1 U to 3 U, from 0.1 U to 2 U, from 0.1 U to 1 U, or from 5 U to 1000 U, from 5 U to 900 U, from 5 U to 800 U, from 5 U to 700 U, from 5 U to 600 U, from 5 U to 500 U, from 5 U to 400 U, from 5 U to 300 U, from 5 U to 200 U, from 5 U to 100 U, from 5 U to 90 U, from 5 U to 80 U, from 5 U to 70 U, from 5 U to 60 U, from 5 U to 50 U, from 5 U to 40 U, from 5 U to 30 U, from 5 U to 20 U, from 5 U to 19 U, from 5 U to 18 U, from 5 U to 17 U, from 5 U to 16 U, from 5 U to 15 U, from 5 U to 14 U, from 5 U to 13 U, from 5 U to 12 U, from 5 U to 11 U, from 5 U to 10 U, or from 10 U to 1000 U, from 10 U to 900 U, from 10 U to 800 U, from 10 U to 700 U, from 10 U to 600 U, from 10 U to 500 U, from 10 U to 400 U, from 10 U to 300 U, from 10 U to 200 U, from 10 U to 100 U, from 10 U to 90 U, from 10 U to 80 U, from 10 U to 70 U, from 10 U to 60 U, from 10 U to 50 U, or from 50 U to 1000 U, from 50 U to 900 U, from 50 U to 800 U, from 50 U to 700 U, from 50 U to 600 U, from 50 U to 500 U, from 50 U to 400 U, from 50 U to 300 U, from 50 U to 200 U, from 50 U to 150 U, or at 100 U per mL preparation.

In a preferred embodiment, preferably of the first aspect of the invention, which is also an embodiment of any other embodiment of the first aspect, the invention relates to a process wherein the amount of nuclease used per gram biomass equivalents treated as disclosed herein, preferably of biomass equivalents of fermentation broth, cell concentrate, homogenate, or any other preparation disclosed herein, and preferably of composition II, is more than 2,000 U, more than 1900 U, more than 1800 U, more than 1700 U, more than 1600 U, more than 1500 U, more than 1400 U, more than 1300 U, more than 1200 U, more than 1100 U, more than 1,000 U, more than 900 U, more than 800 U, more than 700 U, more than 600 U, more than 500 U, more than 400 U, more than 350 U, more than 300 U, more than 250 U, more than 200 U, more than 150 U, more than 100 U, more than 50 U, more than 25 U, more than 10 U, more than 5 U, more than 3 U, more than 2 U, more than 1 U, more than 0.5 U, or more than 0.1 U; or from 0.1 U to 2000 U, from 0.1 U to 1900 U, from 0.1 U to 1800 U, from 0.1 U to 1700 U, from 0.1 U to 1600 U, from 0.1 U to 1500 U, from 0.1 U to 1400 U, from 0.1 U to 1300 U, from 0.1 U to 1200 U, from 0.1 U to 1100 U, from 0.1 U to 1000 U, from 0.1 U to 900 U, from 0.1 U to 800 U, from 0.1 U to 700 U, from 0.1 U to 600 U, from 0.1 U to 500 U, from 0.1 U to 400 U, from 0.1 U to 350 U, from 0.1 U to 300 U; or from 5 U to 2000 U, from 5 U to 1900 U, from 5 U to 1800 U, from 5 U to 1700 U, from 5 U to 1600 U, from 5 U to 1500 U, from 5 U to 1400 U, from 5 U to 1300 U, from 5 U to 1200 U, from 5 U to 1100 U, from 5 U to 1000 U, from 5 U to 900 U, from 5 U to 800 U, from 5 U to 700 U, from 5 U to 600 U, from 5 U to 500 U, from 5 U to 400 U, from 5 U to 350 U, from 5 U to 300 U; or from 10 U to 2000 U, from 10 U to 1900 U, from 10 U to 1800 U, from 10 U to 1700 U, from 10 U to 1600 U, from 10 U to 1500 U, from 10 U to 1400 U, from 10 U to 1300 U, from 10 U to 1200 U, from 10 U to 1100 U, from 10 U to 1000 U, from 10 U to 900 U, from 10 U to 800 U, from 10 U to 700 U, from 10 U to 600 U, from 10 U to 500 U, from 10 U to 400 U, from 10 U to 350 U, from 10 U to 300 U; or from 50 U to 2000 U, from 50 U to 1900 U, from 50 U to 1800 U, from 50 U to 1700 U, from 50 U to 1600 U, from 50 U to 1500 U, from 50 U to 1400 U, from 50 U to 1300 U, from 50 U to 1200 U, from 50 U to 1100 U, from 50 U to 1000 U, from 50 U to 900 U, from 50 U to 800 U, from 50 U to 700 U, from 50 U to 600 U, from 50 U to 500 U, from 50 U to 400 U, from 50 U to 350 U, from 50 U to 300 U; and preferably from 100 U to 300 U, from 120 U to 300 U, from 150 U to 300 U, from 200 U to 300 U, and most preferably from 220 U to 280 U, and utmost preferably of 250 U per gram biomass equivalent.

For the purpose of this invention "biomass equivalent" shall mean the amount of the harvested biomass as "bio wet mass" initially collected from a fermentation broth in gram, and the respective equivalent amounts from such harvested biomass in gram, which are contained in any homogenate, cell-free preparation, or any other partially or fully purified preparation derived from such initially collected harvested biomass, irrespective of the specific volume of such fermentation broth, homogenate, cell-free preparation, or other preparation, and irrespective of whether such fermentation broth, homogenate, cell-free preparation, or other preparation is, diluted, concentrated, or none of both. The "bio wet mass" in the meaning of this invention shall mean the weight in gram of cells, which are pelleted from fermentation broth and separated from supernatant, but without any specific drying of such pelleted cells. For clarification: A fermentation broth with a measured bio wet mass of 200 g/L fermentation broth, may be 3-fold concentrated to a cell concentrate with a biomass equivalent of 600 g/L for cell homogenization, and the homogenate obtained then may be 1.5-fold diluted to a homogenate with a biomass equivalent of 400 g/L for treatment with a nuclease enzyme.

For the purpose of the invention, U means Unit. 1 nuclease Unit is defined as the nuclease amount to liberate 1 μmol of acid-soluble oligosaccharides from salmon sperm DNA equivalent to a Δ260 nm of 1 in 30 min at the pH 8.0 and temperature of 37° C. in 50 mM Tris-HCl, 1 mM MgCl2, 0.1 mg/mL BSA, 1 mg/mL DNA.

Preferably, e.g. in a 13$^{th}$ embodiment of the first aspect of the invention, which is also an embodiment of the first and the second and the third and the fourth and the fifth and the sixth and the embodiment and the eighth and the ninth and the tenth and the eleventh and the twelfth and any other embodiment of the first aspect, the invention relates to a process wherein for the microfiltration step corresponding to step (f), or step (v), of the first embodiment of the first aspect (clause 1), and according to step (h) of the second embodiment of the first aspect (clause 2), involves membrane-based or filter-based methods, or other suitable methods for particle size-dependent separation of a liquid. It is within the scope of the invention that a membrane is used which is characterized by a size exclusion limit of more than 1000 kDa, more than 500 kDa, more than 400 kDa, more than 300 kDa, more than 200 kDa, more than 150 kDa, more than 100 kDa, more than 90 kDa, more than 80 kDa, more than 70 kDa, more than 60 kDa, more than 50 kDa, more than 40 kDa, more than 30 kDa, more than 20 kDa, more than 10 kDa, or more than 5 kDa, and/or a filter, preferably a depth-filter, is used with equivalent molecular weight exclusion properties, and wherein the recombinant enzyme product is obtained in the filtrate of the microfiltration step. For the purpose of the invention kDa means kilodalton.

Preferably, e.g. in a 14$^{th}$ embodiment of the first aspect of the invention, which is also an embodiment of the first and the second and the third and the fourth and the fifth and the sixth and the seventh and the eighth and the ninth and the tenth and the eleventh and the twelfth and the 13$^{th}$ and any other embodiment of the first aspect, the invention relates to a process wherein for the microfiltration step corresponding to step (f), or (v), from the first embodiment of the first aspect (clause 1), and according to step (h) from the second embodiment of the first aspect (clause 2), involves membrane-based or filter-based methods, or other suitable methods for particle size-dependent separation of a liquid. It is within the scope of the invention that a membrane is used with a size exclusion limit of more than 1 μm, more than 4 μm, more than 3 μm, more than 2 μm, more than 1 μm, more than 0.5 μm, more than 0.4 μm, more than 0.3 μm, more than 0.2 μm, or more than 0.1 μm, and/or a filter, preferably a depth-filter, is used with equivalent size exclusion properties, and wherein the recombinant enzyme product is obtained in the filtrate of the microfiltration step.

Preferably, e.g. in a 15$^{th}$ embodiment of the first aspect of the invention, which is also an embodiment of the first and the second and the third and the fourth and the fifth and the sixth and the seventh and the eighth and the ninth and the tenth and the eleventh and the twelfth and the 13$^{th}$ and the 14$^{th}$ and any other embodiment of the first aspect, the invention relates to a process wherein after the microfiltration step corresponding to step (f), or (v), from the first embodiment (clause 1), and corresponding to step (h) from the second embodiment (clause 2), optionally, an additional ultrafiltration step is applied, which ultrafiltration involves membrane-based or filter-based methods, or other suitable methods for particle size-dependent separation of a liquid. It is within the scope of the invention that a membrane is used with a size exclusion limit of more than 100 kDa, more than 80 kDa, more than 60 kDa, more than 50 kDa, more than 40 kDa, more than 30 kDa, more than 20 kDa, more than 15 kDa, more than 10 kDa, more than 5 kDa or more than 1 kDa and/or a filter, preferably a depth-filter, is used with equivalent molecular weight exclusion properties, and wherein the recombinant enzyme product is obtained in the retentate of the ultrafiltration step.

Preferably, the invention relates to a process wherein after the microfiltration step corresponding to step (f), or (v), from the first embodiment (clause 1), and according to step (h) from the second embodiment of the first aspect (clause 2), optionally an additional ultrafiltration step is applied, which ultrafiltration step involves membrane-based or filter-based methods, or other suitable methods for particle size-dependent separation of a liquid. It is within the scope of the invention that a membrane is used with a size exclusion limit of more than 0.1 µm, more than 0.09 µm, more than 0.08 µm, more than 0.07 µm, more than 0.06 µm, more than 0.05 µm, more than 0.04 µm, more than 0.03 µm, more than 0.02 µm, or more than 0.01 µm, and/or a filter, preferably a depth-filter, is used with equivalent size exclusion properties, and wherein the recombinant enzyme product is obtained in the filtrate of the microfiltration step.

Preferably, for the microfiltration step corresponding to step (f), or (v), from the first embodiment (clause 1), and according to step (h) from the second embodiment of the first aspect (clause 2), and/or the optional ultrafiltration step, filtration methods known in the state of the art may be used.

Filtration methods comprise membrane-based or filter-based technologies, enclosing for example tangential-flow filtration, cross-flow filtration, hollow-fiber filtration, filter press with suitable filter or membrane material. Microfiltration usually covers filtration with size exclusion cut-off ranges of higher than 0.1 µm (>0.1 µm), while ultrafiltration usually covers filtration with size exclusion cut-off ranges of lower than 0.1 µm (<0.1 µm).

Preferably, e.g. in a $16^{th}$ embodiment of the first aspect of the invention, which is also an embodiment of the first and the second and the third and the fourth and the fifth and the sixth and the seventh and the eighth and the ninth and the tenth and the eleventh and the twelfth and the $13^{th}$ and the $14^{th}$ and the $15^{th}$ and any other embodiment of the first aspect, the invention relates to a process wherein the solid/liquid separation step corresponding to step (e), or (iv), from the first embodiment (clause 1) and according to step (g) from the second embodiment of the first aspect (clause 2), is realized by techniques of centrifugation, flow centrifugation, filter presses, filtration methods, and/or any other techniques suitable for partial, or complete, separation of liquid phases from solid phases. The methods are chosen based on the volume scale to be processed in the step.

Preferably, the solid/liquid separation step of the process corresponding to step (e), or (iv), from the first embodiment (clause 1) and according to step (g) from the second embodiment of the first aspect (clause 2) follows the step of adding a precipitation agent corresponding to step (d), or (iii), from the first embodiment and according to step (f) from the second embodiment of the first aspect of the invention.

Preferably, e.g. in a $17^{th}$ embodiment of the first aspect of the invention, which is also an embodiment of the first and the second and the third and the fourth and the fifth and the sixth and the seventh and the eighth and the ninth and the tenth and the eleventh and the twelfth and the $13^{th}$ and the $14^{th}$ and the $15^{th}$ and the $16^{th}$ and any other embodiment of the invention, the invention relates to a process wherein at least 5, preferably at least 4, more preferably at least 3, even more preferably at least 2 and most preferred at least 1 intracellular protein(s) is/are expressed.

Preferably, e.g. in a $18^{th}$ embodiment of the first aspect of the invention, which is also an embodiment of the first and the second and the third and the fourth and the fifth and the sixth and the seventh and the eighth and the ninth and the tenth and the eleventh and the twelfth and the $13^{th}$ and the $14^{th}$ and the $15^{th}$ and the $16^{th}$ and the 17th and any other embodiment of the first aspect, the invention relates to a process, wherein the one or more recombinant enzymes expressed from a production strain alone or together make up at least 50%, preferred at least 40%, more preferred at least 30%, more preferred at least 20% even more preferred at least 10%, yet more preferred at least 5%, yet more preferred at least 1%, and most preferred at least 0.1% of the total protein content of the enzyme product.

Preferably, e.g. in a $19^{th}$ embodiment of the first aspect of the invention, which is also an embodiment of the first and the second and the third and the fourth and the fifth and the sixth and the seventh and the eighth and the ninth and the tenth and the eleventh and the twelfth and the $13^{th}$ and the $14^{th}$ and the $15^{th}$ and the $16^{th}$ and the $17^{th}$ and the $18^{th}$ and any other embodiment of the first aspect, the invention relates to a process wherein the enzyme product is a food enzyme. For the purpose of the invention, food enzymes means enzyme that are added to a food stuff, that are used as processing agents for the preparation or processing of food stuff, or which are used for a downstream enzymatic conversion for the manufacturing of a food ingredient. For food enzymes, manufacturing quality standards have been defined, requiring compliance with certain specification, including for example the specifications and recommended purity criteria set forth in the Food Chemicals or equivalent international food or pharmacopeia standard [e.g., JECFA, Food Chemical Codex (FCC), United States Pharmacopeia (USP), European Pharmacopeia (EP)], cGMP for food and/or the principles of Hazard Analysis of Critical Control Points (HACCP).

Preferably, e.g. in a $20^{th}$ embodiment of the first aspect of the invention, which is also an embodiment of the first and the second and the third and the fourth and the fifth and the sixth and the embodiment and the eighth and the ninth and the tenth and the eleventh and the twelfth and the $13^{th}$ and the $14^{th}$ and the $15^{th}$ and the $16^{th}$ and the $17^{th}$ and the $18^{th}$ and the $19^{th}$ and any other embodiment of the first aspect, the invention relates to a process, wherein the enzyme product is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases. Enzymes from such classes are well described in the state of the art, for example in the SEQ ID NOs of the patent application WO 2008/151807, WO 2012/048865, WO 2015/162064, WO 2016/198660, or WO 2016/198665, which SEQ ID NOs herein are introduced as reference to the disclosure of this invention.

Preferably, e.g. in a $21^{st}$ embodiment of the first aspect of the invention, which is also an embodiment of the first and the second and the third and the fourth and the fifth and the sixth and the seventh and the eighth and the ninth and the tenth and the eleventh and the twelfth and the $13^{th}$ and the $14^{th}$ and the $15^{th}$ and the $16^{th}$ and the $17^{th}$ and the $18^{th}$ and the 19th and the 20th embodiment of the first aspect, the invention relates to a process, wherein the enzyme product is selected from the group consisting of a. carbohydrate-modifying enzymes, such as glycosyl hydrolases, glycosyltransferases, polysaccharide lyases, carbohydrate esterases;
b. amino acid, peptide or protein-modifying enzymes, such as aminotransferases, proteases and peptidases; and
c. lipid modifying enzymes such as lipases or phospholipases.

For the purpose of the invention, a carbohydrate modifying enzyme is an enzyme that performs its catalytic activity on a substrate that (i) is a carbohydrate or a carbohydrate derivative or that (ii) forms a carbohydrate or carbohydrate derivative as product along with its catalytic activity. Carbohydrate modifying enzymes are very useful enzymes for the food industry. They for instance can be used for the synthesis of carbohydrate food ingredients in downstream enzyme conversion.

Preferably, e.g. in a 22nd embodiment of the first aspect of the invention, which is also an embodiment of the first and the second and the third and the fourth and the fifth and the sixth and the seventh and the eighth and the ninth and the tenth and the eleventh and the twelfth and the 13th and the 14th and the 15th and the 16th and the 17th and the 18th and the 19th and the 20th and the 21st and any other embodiment of the first aspect, the invention relates to a process, wherein the enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

Preferably, e.g. in a 23rd embodiment of the first aspect of the invention, which is also an embodiment of the first and the second and the third and the fourth and the fifth and the sixth and the seventh and the eighth and the ninth and the tenth and the eleventh and the twelfth and the 13th and the 14th and the 15th and the 16th and the 17th and the 18th and the 19th and the 20th and the 21st and the 22nd and any other embodiment of the first aspect, the invention relates to a process, wherein the microbial production host is modified by deletion of one or more additional genes selected from the group consisting of, for example, the genes encoding the enzymes, preferably the E. coli enzymes, phophosglucomutase, alkaline phosphatase, glucose-1-phosphate phosphatase, UDP-glucose 6-dehydrogenase, cellulose synthase (UDP-forming), alpha,alpha-trehalose-phosphate synthase (UDP-forming), UDP-glucose-hexose-1-phosphate uridylyltransferase, UTP-glucose-1-phosphate uridylyltransferase, UTP-glucose-1-phosphate uridylyltransferase, UDP-sugar diphosphatase, nucleotide diphosphatase, UDP-glucose 4-epimerase, ribonucleoside-diphosphate reductase, ribonucleoside-diphosphate reductase, lipopolysaccharide N-acetylmannosaminouronosyltransferase, lipid-A-disaccharide synthase, undecaprenyldiphospho-muramoylpentapeptide beta-N-acetylglucosaminyltransferase, undecaprenyl-phosphate 4-deoxy-4-formamido-L-arabinose transferase, 6-phosphofructokinase, pyruvate kinase, uridine kinase, UMP kinase, nucleoside-diphosphate kinase, polyribonucleotide nucleotidyltransferase, UDP-N-acetylglucosamine 2-epimerase (non-hydrolysing), beta-galactosidase, N-acetylneuraminate lyase, N-acetylmannosamine kinase, putative N-acetylmannosamine-6-phosphate 2-epimerase, alpha-galactosidase, galactoside O-acetyltransferase.

The crude enzyme preparation of a recombinant enzyme might contain side activities of enzymes coming from the metabolism of the production hosts. For carbohydrate-modifying enzymes, such interference side enzyme activities may derive from the carbohydrate metabolism, for enzymes requiring activated carbohydrate moieties, being linked with nucleotide mono-, di- or tri-phosphates, e.g. of the nucleotides adenosine, uridine, cytidine, guanosine, such interference side enzyme activities may derive from the carbohydrate and/or nucleotide metabolism. In a preferred embodiment corresponding carbohydrate modifying enzyme genes from the host are deleted are inactivated by genetic engineering or DNA Editing methods. Such gene deletions or inactivation can comprise one or several genes selected from the group consisting of, for example, the genes encoding the enzymes, preferably the E. coli enzymes, phophosglucomutase, alkaline phosphatase, glucose-1-phosphate phosphatase, UDP-glucose 6-dehydrogenase, cellulose synthase (UDP-forming), alpha,alpha-trehalose-phosphate synthase (UDP-forming), UDP-glucose-hexose-1-phosphate uridylyltransferase, UTP-glucose-1-phosphate uridylyltransferase, UTP-glucose-1-phosphate uridylyltransferase, UDP-sugar diphosphatase, nucleotide diphosphatase, UDP-glucose 4-epimerase, ribonucleoside-diphosphate reductase, ribonucleoside-diphosphate reductase, lipopolysaccharide N-acetylmannosaminouronosyltransferase, lipid-A-disaccharide synthase, undecaprenyldiphospho-muramoylpentapeptide beta-N-acetylglucosaminyltransferase, undecaprenyl-phosphate 4-deoxy-4-formamido-L-arabinose transferase, 6-phosphofructokinase, pyruvate kinase, uridine kinase, UMP kinase, nucleoside-diphosphate kinase, polyribonucleotide nucleotidyltransferase, UDP-N-acetylglucosamine 2-epimerase (non-hydrolysing), beta-galactosidase, N-acetylneuraminate lyase, N-acetylmannosamine kinase, putative N-acetylmannosamine-6-phosphate 2-epimerase, alpha-galactosidase, galactoside O-acetyltransferase.

Preferably, e.g. in a 24th embodiment of the first aspect of the invention, which is also an embodiment of the first and the second and the third and the fourth and the fifth and the sixth and the seventh and the eighth and the ninth and the tenth and the eleventh and the twelfth and the 13th and the 14th and the 15th and the 16th and the 17th and the 18th and the 19th and the 20th and the 21st and the 22nd and the 23rd and any other embodiment of the first aspect, the invention relates to a process, wherein the process comprises the following steps:

a. treatment of a cell disruption crude lysate containing recombinant enzyme products with a nuclease, thereby providing a composition II comprising recombinant enzyme products, broken nucleic acids, and optionally cell debris;
b. addition of a precipitation agent to complex nucleic acids, thereby providing a composition III comprising the enzyme products, complexed broken down nucleic acids, and optionally the cell debris;
c. liquid/solid separation to remove cell debris and nucleic acid/precipitation agent complexes from the liquid phase, thereby providing a separated solid phase comprising the complexed broken down nucleic acids and optionally the cell debris and a liquid composition IV comprising the enzyme products; and
d. conducting a microfiltration step to remove residual solids, and/or high molecular weight components, thereby providing a composition V comprising the enzyme products.

In another embodiment, the invention relates to a process for the manufacture of a recombinant enzyme formulation, wherein after the solid/liquid separation in step (iv) the separated solid phase comprises primarily complexed broken down nucleic acids, and optionally the cell debris, and optionally remainders of the enzyme product derived from composition III; and wherein the separated liquid phase obtained, in particular composition IV, comprises primarily the enzyme product, and optionally remainders of cell debris and complexed broken down nucleic acids derived from composition III.

In a preferred embodiment, preferably of the first aspect of the invention, which is also an embodiment of any of the previous embodiments of the first aspect, the process is characterized by a. a reduction of nucleic acids content in composition V in comparison to composition I; and/or b. a recovery of catalytic activity of the enzyme product in composition V in comparison to composition I.

In a preferred embodiment, preferably of the first aspect of the invention, which is also an embodiment of any of the previous embodiments hereof, the process is characterized by a reduction of nucleic acids content in composition V, or optionally in composition VI, in comparison to composition I by a factor from 2 to 100 million, from 2 to 50 million, from 2 to 30 million, from 2 to 20 million, from 2 to 15 million, from 2 to 10 million, from 100 to 100 million, from 100 to 50 million, from 100 to 30 million, from 100 to 20 million, from 100 to 15 million, from 100 to 10 million, from 1000 to 100 million, from 1000 to 50 million, from 1000 to 30 million, from 1000 to 20 million, from 1000 to 15 million, from 1000 to 10 million, from 10,000 to 100 million, from 10,000 to 50 million, from 10,000 to 30 million, from 10,000 to 20 million, from 10,000 to 15 million, from 10,000 to 10 million, from 100,000 to 100 million, from 100,000 to 50 million, from 100,000 to 30 million, from 100,000 to 20 million, from 100,000 to 15 million, from 100,000 to 10 million, from 1 million to 100 million, from 1 million to 50 million, from 1 million to 30 million, from 1 million to 20 million, from 1 million to 15 million, from 1 million to 10 million.

In a preferred embodiment, preferably of the first aspect of the invention, which is also an embodiment of any of the previous embodiments hereof, the process is characterized by a nucleic acids content in an enzyme product, composition V, or optionally in a composition VI, that is characterized by a DNA concentration per enzyme product, or per composition V, or per composition VI, of from 0.01 ng/g to 50 ng/g, of from 0.01 ng/g to 40 ng/g, of from 0.01 ng/g to 30 ng/g, of from 0.01 ng/g to 20 ng/g, of from 0.01 ng/g to 10 ng/g, of from 0.01 ng/g to 9 ng/g, of from 0.01 ng/g to 8 ng/g, of from 0.01 ng/g to 7 ng/g, of from 0.01 ng/g to 6 ng/g, of from 0.01 ng/g to 5 ng/g, of from 0.01 ng/g to 4 ng/g, of from 0.01 ng/g to 3 ng/g, of from 0.01 ng/g to 2 ng/g, of from 0.01 ng/g to 1 ng/g, and preferably of from 0.01 ng/g to 0.9 ng/g, of from 0.01 ng/g to 0.8 ng/g of from 0.01 ng/g to 0.7 ng/g of from 0.01 ng/g to 0.6 ng/g of from 0.01 ng/g to 0.5 ng/g, of from 0.01 ng/g to 0.4 ng/g, of from 0.01 ng/g to 0.3 ng/g, of from 0.01 ng/g to 0.2 ng/g, of from 0.01 ng/g to 0.1 ng/g, or preferably of from 0.001 ng/g to 50 ng/g, of from 0.001 ng/g to 40 ng/g, of from 0.001 ng/g to 30 ng/g, of from 0.001 ng/g to 20 ng/g, of from 0.001 ng/g to 10 ng/g, of from 0.001 ng/g to 9 ng/g, of from 0.001 ng/g to 8 ng/g, of from 0.001 ng/g to 7 ng/g, of from 0.001 ng/g to 6 ng/g, of from 0.001 ng/g to 5 ng/g, of from 0.001 ng/g to 4 ng/g, of from 0.001 ng/g to 3 ng/g, of from 0.001 ng/g to 2 ng/g, of from 0.001 ng/g to 1 ng/g, and preferably of from 0.001 ng/g to 0.9 ng/g, of from 0.001 ng/g to 0.8 ng/g of from 0.001 ng/g to 0.7 ng/g of from 0.001 ng/g to 0.6 ng/g of from 0.001 ng/g to 0.5 ng/g, of from 0.001 ng/g to 0.4 ng/g, of from 0.001 ng/g to 0.3 ng/g, of from 0.001 ng/g to 0.2 ng/g, of from 0.001 ng/g to 0.1 ng/g, or more preferably of from 0 ng/g to 50 ng/g, of from 0 ng/g to 40 ng/g, of from 0 ng/g to 30 ng/g, of from 0 ng/g to 20 ng/g, of from 0 ng/g to 10 ng/g, of from 0 ng/g to 9 ng/g, of from 0 ng/g to 8 ng/g, of from 0 ng/g to 7 ng/g, of from 0 ng/g to 6 ng/g, of from 0 ng/g to 5 ng/g, of from 0 ng/g to 4 ng/g, of from 0 ng/g to 3 ng/g, of from 0 ng/g to 2 ng/g, of from 0 ng/g to 1 ng/g, and more preferably of from 0 ng/g to 0.9 ng/g, of from 0 ng/g to 0.8 ng/g of from 0 ng/g to 0.7 ng/g of from 0 ng/g to 0.6 ng/g of from 0 ng/g to 0.5 ng/g, of from 0 ng/g to 0.4 ng/g, from 0 ng/g to 0.3 ng/g, from 0 ng/g to 0.2 ng/g, or of 0 ng/g to 0.1 ng/g, and most preferably of from 0 ng/g to 0.09 ng/g, of from 0 ng/g to 0.08 ng/g of from 0 ng/g to 0.07 ng/g of from 0 ng/g to 0.06 ng/g of from 0 ng/g to 0.05 ng/g, of from 0 ng/g to 0.04 ng/g, from 0 ng/g to 0.03 ng/g, from 0 ng/g to 0.02 ng/g, from 0 ng/g to 0.01 ng/g, and most preferably of below 0.1 ng/g, or utmost preferably of below 0.01 ng/g, each in respect to the direct enzyme product, the composition V, or the composition VI, or any liquid, lyophilized, or stabilized formulation derived therefrom.

In a preferred embodiment, preferably of the first aspect of the invention, which is also an embodiment of any of the previous embodiments hereof, the process is characterized by a recovery of catalytic activity of the enzyme product in composition V, or optionally in composition VI, is comparison to composition I by a rate of at least 1% up to 100%, of at least 5% up to 100%, of at least 10% up to 100%, of at least 15% up to 100%, of at least 20% up to 100%, of at least 25% up to 100%, of at least 30% up to 100%, of at least 35% up to 100%, of at least 40% up to 100%, of at least 45% up to 100%, of at least 50% up to 100%, of at least 55% up to 100%, of at least 60% up to 100%, of at least 65% up to 100%, of at least 70% up to 100%, of at least 75% up to 100%, of at least 80% up to 100%, of at least 85% up to 100%, of at least 90% up to 100%, of at least 95% up to 100%, or of at least 96% up to 100%, of at least 97% up to 100%, of at least 98% up to 100%, of at least 99% up to 100%, more preferably of at least 25% up to 99%, of at least 30% up to 99%, of at least 35% up to 99%, of at least 40% up to 99%, of at least 45% up to 99%, of at least 50% up to 99%, of at least 55% up to 99%, of at least 60% up to 99%, of at least 65% up to 99%, of at least 70% up to 99%, of at least 75% up to 99%, of at least 80% up to 99%, of at least 85% up to 99%, of at least 90% up to 99%, of at least 95% up to 99%, or of at least 96% up to 99%, of at least 97% up to 99%, of at least 98% up to 99%, even more preferably of at least 25% up to 95%, of at least 30% up to 95%, of at least 35% up to 95%, of at least 40% up to 95%, of at least 45% up to 95%, of at least 50% up to 95%, of at least 55% up to 95%, of at least 60% up to 95%, of at least 65% up to 95%, of at least 70% up to 95%, of at least 75% up to 95%, of at least 80% up to 95%, of at least 85% up to 95%, of at least 90% up to 95%, even more preferably of at least 50% up to 90%, of at least 55% up to 90%, of at least 60% up to 90%, of at least 65% up to 90%, of at least 70% up to 90%, of at least 75% up to 90%, of at least 80% up to 90%, of at least 85% up to 90%, even more preferably of at least 55% up to 85%, of at least 60% up to 85%, of at least 65% up to 85%, of at least 70% up to 85%, of at least 75% up to 85%, of at least 80% up to 85%, most preferably of at least of at least 60% up to 80%, of at least 65% up to 80%, of at least 70% up to 80%, of at least 75% up to 80%.

The invention also relates to a recombinant enzyme preparation obtainable by the process according to the invention.

Preferably, the preparation is characterized by a residual DNA concentration of from 0 ng/g to 50 ng/g, of from 0 ng/g to 40 ng/g, of from 0 ng/g to 30 ng/g, of from 0 ng/g to 20 ng/g, of from 0 ng/g to 10 ng/g, of from 0 ng/g to 9 ng/g, of from 0 ng/g to 8 ng/g, of from 0 ng/g to 7 ng/g, of from 0 ng/g to 6 ng/g, of from 0 ng/g to 5 ng/g, of from 0 ng/g to 4 ng/g, of from 0 ng/g to 3 ng/g, of from 0 ng/g to 2 ng/g, of from 0 ng/g to 1 ng/g, and preferably of from 0 ng/g to 0.9 ng/g, of from 0 ng/g to 0.8 ng/g of from 0 ng/g to 0.7 ng/g of from 0 ng/g to 0.6 ng/g of from 0 ng/g to 0.5 ng/g, of from 0 ng/g to 0.4 ng/g, of from 0 ng/g to 0.3 ng/g, of from 0 ng/g to 0.2 ng/g, and of from 0 ng/g to 0.1 ng/g, or more preferably of below 0.1 ng/g, or most preferably of below 0.01 ng/g.

In a second aspect of the invention, the invention relates to a preparation of enzyme products, which have been manufactured according to the first aspect of the invention, or to any of the embodiments of the first aspect of the invention.

Preferably, e.g. in a first embodiment of the second aspect of the invention, the invention relates to a preparation of an enzyme product, which has been manufactured according to the first aspect of the invention, or to any of the embodiments of the first aspect of the invention, and which is characterized by a residual DNA concentration in the enzyme product, or composition V, or composition VI, of from 0.01 ng/g to 50 ng/g, of from 0.01 ng/g to 40 ng/g, of from 0.01 ng/g to 30 ng/g, of from 0.01 ng/g to 20 ng/g, of from 0.01 ng/g to 10 ng/g, of from 0.01 ng/g to 9 ng/g, of from 0.01 ng/g to 8 ng/g, of from 0.01 ng/g to 7 ng/g, of from 0.01 ng/g to 6 ng/g, of from 0.01 ng/g to 5 ng/g, of from 0.01 ng/g to 4 ng/g, of from 0.01 ng/g to 3 ng/g, of from 0.01 ng/g to 2 ng/g, of from 0.01 ng/g to 1 ng/g, and preferably of from 0.01 ng/g to 0.9 ng/g, of from 0.01 ng/g to 0.8 ng/g, of from 0.01 ng/g to 0.7 ng/g, of from 0.01 ng/g to 0.6 ng/g, of from 0.01 ng/g to 0.5 ng/g, of from 0.01 ng/g to 0.4 ng/g, of from 0.01 ng/g to 0.3 ng/g, of from 0.01 ng/g to 0.2 ng/g, of from 0.01 ng/g to 0.1 ng/g, or more preferably of from 0.001 ng/g to 50 ng/g, of from 0.001 ng/g to 40 ng/g, of from 0.001 ng/g to 30 ng/g, of from 0.001 ng/g to 20 ng/g, of from 0.001 ng/g to 10 ng/g, of from 0.001 ng/g to 9 ng/g to 8 ng/g, of from 0.001 ng/g to 7 ng/g, of from 0.001 ng/g to 6 ng/g, of from 0.001 ng/g to 5 ng/g, of from 0.001 ng/g to 4 ng/g, of from 0.001 ng/g to 3 ng/g, of from 0.001 ng/g to 2 ng/g, of from 0.001 ng/g to 1 ng/g, and preferably of from 0.001 ng/g to 0.9 ng/g, of from 0.001 ng/g to 0.8 ng/g, of from 0.001 ng/g to 0.7 ng/g, of from 0.001 ng/g to 0.6 ng/g, of from 0.001 ng/g to 0.5 ng/g, of from 0.001 ng/g to 0.4 ng/g, of from 0.001 ng/g to 0.3 ng/g, of from 0.001 ng/g to 0.2 ng/g, of from 0.001 ng/g to 0.1 ng/g, or even more preferably of from 0 ng/g to 50 ng/g, of from 0 ng/g to 40 ng/g, of from 0 ng/g to 30 ng/g, of from 0 ng/g to 20 ng/g, of from 0 ng/g to 10 ng/g, of from 0 ng/g to 9 ng/g, of from 0 ng/g to 8 ng/g, of from 0 ng/g to 7 ng/g, of from 0 ng/g to 6 ng/g, of from 0 ng/g to 5 ng/g, of from 0 ng/g to 4 ng/g, of from 0 ng/g to 3 ng/g, of from 0 ng/g to 2 ng/g, of from 0 ng/g to 1 ng/g, and preferably of from 0 ng/g to 0.9 ng/g, of from 0 ng/g to 0.8 ng/g, of from 0 ng/g to 0.7 ng/g, of from 0 ng/g to 0.6 ng/g, of from 0 ng/g to 0.5 ng/g, of from 0 ng/g to 0.4 ng/g, of from 0 ng/g to 0.3 ng/g, of from 0 ng/g to 0.2 ng/g, of from 0 ng/g to 0.1 ng/g, or most preferably of below 0.1 ng/g, or utmost preferably of below 0.01 ng/g in respect to the direct enzyme product, the composition V, or the composition VI, or in any liquid, lyophilized, and stabilized formulation derived therefrom.

For the purpose of this invention, the recombinant DNA concentration is to be determined by a method based on a polymerase Chain Reaction (PCR) based amplification of a representative DNA fragment comprising recombinant DNA of a size of at least 50 to 5,000 base pairs, or of at least 100 to 5,000 base pairs, or of at least 1,000 to 5,000 base pairs, or of complete enzyme gene sequences. The calibration is done with a total DNA preparation from the production host. Standard PCR techniques, including real-time PCR, may be used for determination of recombinant DNA concentration, wherein PCR primers may be directed against the microbial host DNA and/or expression vector DNA.

The concentration of residual DNA within a product or preparation can further be determined by methods established in the state of the art. For the preparation of food enzymes, for example, possible methods to be accomplished are described in EFSA Journal 2011; 9(6):2193 or any document update that may be published by EFSA in the future.

It is within the scope of the invention that the residual DNA concentration of the invention is determined by use of a method selected from or based on the guidance taken from EFSA Journal 2011; 9(6):2193], which is herein introduced as reference.

In a preferred embodiment, preferably of the second aspect of the invention, or any of the embodiments of the second aspect, relates to a preparation of an enzyme product, which has been manufactured according to the first aspect of the invention, or to any of the embodiments of the first aspect of the invention, wherein the enzyme product can be distinguished from other preparations by the absence of DNA fragments in the preparation of the enzyme product.

Preferably, e.g. in a second embodiment of the second aspect of the invention, which is also an embodiment of the first and any other embodiment of the second aspect, the invention relates to a preparation of an enzyme product, which has been manufactured according to the first aspect of the invention, or to any of the embodiments of the first aspect of the invention, wherein the enzyme product is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases.

Preferably, e.g. in a third embodiment of the second aspect of the invention, which is also an embodiment of the first and the second and any other embodiment of the second aspect, the invention relates to a preparation of an enzyme product, which has been manufactured according to the first aspect of the invention, or to any of the embodiments of the first aspect of the invention, wherein the enzyme product is selected from the group consisting of a. carbohydrate-modifying enzymes, such as glycosyl hydrolases, glycosyltransferases, polysaccharide lyases, carbohydrate esterases;

b. amino acid, peptide or protein-modifying enzymes, such as aminotransferases, proteases and peptidases; and c. lipid modifying enzymes such as lipases or phospholipases.

Preferably, e.g. in a fourth embodiment of the second aspect of the invention, which is also an embodiment of the first and the second and the third and any other embodiment of the second aspect, the invention relates to a preparation of an enzyme product, which has been manufactured according to the first aspect of the invention, or to any of the embodiments of the first aspect of the invention, wherein the enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

Preferably, the invention relates to a preparation of an enzyme product, which has been manufactured according to the first aspect of the invention, or to any of the embodiments of the first aspect of the invention, wherein the enzyme product is a glycosyl-transferase, i.e. UDP-glycosyl-transferase (2.4.1.X), or a sucrose synthase (EC 2.4.1.13). Preferably, the enzyme product is a wild-type enzyme known or any improved variants derived therefrom by enzyme engineering technologies.

It is within the scope of this invention, that enzyme products manufactured by use of the invention may be wild-type enzymes known or any improved variants derived therefrom by enzyme engineering technologies.

The invention also relates to a process for the manufacture of an enzyme preparation comprising the steps of
A) providing *E. coli* strains;
B) optionally, adding nutrient media;
C) fermentation thereby obtaining a fermentation broth;
D) optionally, solid/liquid separation of the fermentation broth thereby obtaining biomass;
E) optionally, homogenization;
F) treatment with nuclease; optionally followed by addition of a precipitating agent;
G) solid/liquid separation thereby obtaining a supernatant; and
H) optionally, filtration thereby obtaining the enzyme preparation.

In a third aspect of the invention, the invention relates to an enzyme preparation of a recombinant intracellularly expressed enzyme.

Preferably, e.g. in a first embodiment of the third aspect of the invention, the invention relates to an enzyme preparation of a recombinant intracellularly expressed enzyme, wherein the enzyme preparation contains a recombinant DNA concentration of less than 50 ng/g, and wherein it contains at least 1 different intracellular host cell proteins of the production host which make up at least 0.1% of the total protein content of the enzyme preparation.

In a preferred embodiment, preferably of the third aspect of the invention, which is also an embodiment of the first embodiment of the first aspect, the invention relates to an enzyme preparation of a recombinant intracellularly expressed enzyme, wherein the enzyme preparation contains a recombinant DNA concentration of less than 50 ng/g, of less than 40 ng/g, of less than 30 ng/g, of less than 20 ng/g, of less than 10 ng/g, of less than 5 ng/g, of less than 1 ng/g, and preferably of less than 0.5 ng/ml, of less than 0.4 ng/ml, of less than 0.3 ng/ml, of less than 0.2 ng/ml, of less than 0.1 ng/ml, and most preferably of less than 0.09 ng/ml, of less than 0.08 ng/ml, of less than 0.07 ng/ml, of less than 0.06 ng/ml, of less than 0.05 ng/ml, of less than 0.04 ng/ml, of less than 0.03 ng/ml, of less than 0.02 ng/ml, of less than 0.01 ng/ml and utmost preferably of 0 ng/ml.

In a preferred embodiment, preferably of the third aspect of the invention, which is also an embodiment of the first embodiment and any other embodiment of the first aspect, the invention relates to an enzyme preparation of a recombinant intracellularly expressed enzyme, wherein the enzyme preparation contains at least 1 or more, at least 2 or more, at least 3 or more, at least 4 or more, or at least 5 or more different intracellular host cell proteins, and preferably contains 1, 2, 3, 4, or 5 different intracellular host cell proteins.

In a preferred embodiment, preferably of the third aspect of the invention, which is also an embodiment of the first embodiment and any other embodiment of the first aspect, the invention relates to an enzyme preparation of a recombinant intracellularly expressed enzyme, wherein the enzyme preparation contains at least 1 or more different intracellular host cell proteins, which make up at least 0.1%, at least 1%, at least 5%, at least 10%, at least 20%, at least 30%, at least 40%, at least 50%, at least 60%, at least 70%, at least 80%, at least 90%, at least 95%, or at least 99% of the total protein content of the enzyme preparation.

In a preferred embodiment, preferably of the third aspect of the invention, which is also an embodiment of the first embodiment and any other embodiment of the first aspect, the invention relates to an enzyme preparation of a recombinant intracellularly expressed enzyme, wherein the enzyme preparation contains a recombinant DNA concentration of less than 50 ng/g, and wherein it contains at least 3 different intracellular host cell proteins of the production host which make up at least 10% of the total protein content of the enzyme preparation.

Preferably, e.g. in a second embodiment of the third aspect of the invention, which is also an embodiment of the first or and any other embodiment of the third aspect, the invention relates to an enzyme preparation of a recombinant intracellularly expressed enzyme, wherein the enzyme preparation is manufactured in the production host *Escherichia coli*.

Preferably, e.g. in a third embodiment of the third aspect of the invention, which is also an embodiment of the first and the second and any other embodiment of the third aspect, the invention relates to an enzyme preparation of a recombinant intracellularly expressed enzyme, wherein the enzyme preparation contains the expressed enzyme product and in addition contains detectable amounts of a nuclease with an identity of at least 70% to the nuclease of SEQ ID NO:1 or SEQ ID NO:2.

In a preferred embodiment, preferably of the third aspect of the invention, or any of the embodiments of the third aspect, the invention relates to an enzyme preparation of recombinant intracellularly expressed enzyme, wherein the enzyme preparation can be distinguished from other enzyme preparations by the absence of DNA fragments in the enzyme product.

Preferably, e.g. in a fourth embodiment of the third aspect of the invention, which is also an embodiment of the first and the second and the third and any other embodiment of the third aspect, the invention relates to an enzyme preparation of a recombinant intracellularly expressed enzyme, wherein the enzyme preparation is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyl-transferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases.

Preferably, e.g. in a fifth embodiment of the third aspect of the invention, which is also an embodiment of the first and the second and the third and the fourth and any other embodiment of the third aspect, the invention relates to an enzyme preparation, wherein the enzyme preparation is selected from the group consisting of
a. carbohydrate-modifying enzymes, such as glycosyl hydrolases, glycosyltransferases, polysaccharide lyases, carbohydrate esterases;
b. amino acid, peptide or protein-modifying enzymes, such as aminotransferases, proteases and peptidases; and
c. lipid modifying enzymes such as lipases or phospholipases.

Preferably, e.g. in a sixth embodiment of the third aspect of the invention, which is also an embodiment of the first and the second and the third and the fourth and the fifth and any other embodiment of the third aspect, the invention relates to an enzyme preparation in which the recombinant enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

DESCRIPTION OF VARIOUS AND PREFERRED EMBODIMENTS

Further preferred embodiments of the invention and their combinations with one another are summarized as Clause 1 to Clause 32 hereinafter:

Clause 1: A process to manufacture a food-grade enzyme product that comprises the following steps: a.) intracellular expression of a recombinant enzyme in a microbial host; b.) release of the recombinant enzyme by cell disruption resulting in a crude lysate; c.) addition of a nuclease to break down nucleic acids in the enzyme product containing process solution resulting in an enzyme-treated lysate; d.) addition of a precipitation agent to complex nucleic acids resulting in a complexed lysate; e.) liquid/solid separation to remove cell debris and nucleic acid/precipitation agent complexes from the liquid phase resulting in a cleared lysate; and f.) conducting a microfiltration step to remove residual solids, and/or high molecular weight components resulting in a filtrate; preferably wherein the process does not involve after the liquid/solid separation step e., and/or after the microfiltration step f.) a treatment of the crude lysate, or the filtrate, respectively, with a nuclease enzyme.

Clause 2: A process for the manufacture of a recombinant enzyme product, which is characterized that comprises one or more of the following steps: a.) cloning of an enzyme product gene into an expression vector; b.) introducing the expression vector carrying the enzyme product gene into a microbial host; c.) fermentation of the microbial host of step (b) under conditions of intracellular expression of the recombinant enzyme product; d.) disrupting the fermented cells of step c. by cell disruption for releasing of the recombinant enzyme product resulting in a crude lysate containing recombinant enzyme product; e.) incubation of the cleared lysate with a nuclease in order to break down nucleic acids from the cleared lysate resulting in an enzyme-treated lysate; f.) addition of a precipitation agent to the lysate for the formation of complexes of nucleic acids resulting in a complexed lysate containing recombinant enzyme product; g.) liquid and/or solid separation of the complexed lysate to remove cell debris and complexes of nucleic acid and precipitation agent from the liquid phase, resulting in a cleared lysate containing recombinant enzyme product; and h.) submission of the enzyme-treated lysate to a microfiltration step to remove residual solids and/or high molecular weight components; preferably wherein the process does not involve after the liquid/solid separation step g., and/or after the microfiltration step h. a treatment of the crude lysate, or the filtrate, respectively, with a nuclease enzyme.

Clause 3: The process according to any of clauses 1 or 2, wherein the microbial host is *Escherichia coli*, preferably a genetically modified derivative strain of the laboratory strain *E. coli* K-12 W3110, and most preferably is LE1B109.

Clause 4: The process according to any of clauses 1 to 3, wherein the expression vectors are based on the vector pRSF-1b.

Clause 5: The process according to any of clauses 1 to 4, wherein the expression vector does not carry antibiotic resistance genes.

Clause 6: The process according to any of the clauses 1 to 5, wherein a suitable antifoam agent is added in step (a) of Clause 1 or in step (c) of Clause 2, wherein the antifoam agent is selected from the group consisting of the antifoam agents polypropylene glycol (CAS Reg No. 25322-69-4), polyglycerolpolyethylene-polypropylene block copolymer (CAS Reg. No. 78041-14-2), polyoxyethylene-polyoxypropylene block copolymer (CAS Reg No. 9003-11-6), polypropylene glycerol monobutyl ether (CAS Reg No. 9003-13-8), polydimethylsiloxane (CAS Reg No. 63148-62-9; CAS Reg No. 68083-18-1), silica (CAS Reg No. 7631-86-9; CAS Reg No. 63231-67-4), stearic acid (CAS Reg No. 57-11-4), sorbitan sesquioleate (CAS Reg No. 8007-43-0), glycerol monostearate (CAS Reg No. 123-94-4), polysorbates (polyoxyethylene sorbitan fatty acid esters like polysorbate 60 (CAS Reg No. 9005-67-8), polysorbate 65 (CAS Reg. No. 9005-71-4), and polysorbate 80 (CAS Reg No. 9005-65-6), rape oil mono- and diglycerides (CAS Reg No. 93763-31-6), and white mineral oil (CAS Reg No. 64742-47-8).

Clause 7: The process according to any of the clauses 1 to 6, wherein one or more suitable flocculants is/are added in step (d) of Clause 1 or in step (f) of Clause 2, wherein the flocculants are selected from the group consisting of the flocculants of a.) cationic polyamine-based flocculants, including dimethylamine-epichlorohydrin copolymer (CAS Reg No. 25988-97-0), methylamine-epichlorohydrin copolymer (CAS Reg No. 31568-35-1), dimethylamine-epichlorohydrin-ethylenediamine terpolymer (CAS Reg No. 42751-79-1); b.) cationic polyacrylamide-based flocculants, including polyacrylamide modified by condensation with formaldehyde and dimethylamine (CAS Reg No. 67953-80-4), acrylamide-acryloxyethyl-trimethyl-ammonium chloride copolymer (CAS Reg No. 69418-26-4); c.) anionic polyamine based flocculants, including acrylamide-acrylic acid copolymer (CAS Reg No. 25987-30-8; CAS Reg No. 9003-06-9); d.) ammonium sulfate (CAS Reg No. 10043-01-3); e.) calcium chloride (CAS Reg No. 10035-04-8; CAS Reg No. 10043-52-4).

Clause 8: The process according to any of the clauses 1 to 7, wherein the precipitation agent is selected from the group consisting of polyethylenimines and polydiallyldimethyl ammonium chloride.

Clause 9: The process according to any of the clauses 1 to 8, wherein the precipitation agent is selected from the group consisting of the precipitation agents Superfloc® 781 G, Superfloc® C448, Superfloc® C581 G, Superfloc® C752, Superfloc® SD-2081, and polyethylenimine Lupasol®.

Clause 10: The process according to any of the clauses 1 to 9 wherein the nuclease used is selected from the group consisting of endonucleases, exonucleases, or mixed exo/endonucleases.

Clause 11: The process according to any of the clauses 1 to 10 wherein the functionally active nuclease used is at least 70%, 75%, 80%, 85%, 90%, 95%, 98%, or 99%, identical to the sequence of SEQ ID NO:1 or SEQ ID NO:2.

Clause 12: The process according to any of the clauses 1 to 11, wherein the amount of nuclease used per ml of fermentation broth is more than 200 U, more than 100 U, more than 50 U, more than 40 U, more than 30 U, more than 20 U, more than 15 U, more than 10 U, more than 5 U, more than 3 U, more than 2 U, more than 1 U, more than 0.5 U or more than 0.1 U.

Clause 13: The process according to any of the clauses 1 to 12 wherein for the microfiltration step corresponding to step (f) from clause 1 and according to step (h) from clause 2, a membrane is used, which is characterized by a size exclusion limit of more than 1000 kDa, more than 500 kDa, more than 400 kDa, more than 300 kDa, more than 200 kDa, more than 150 kDa, more than 100 kDa, more than 90 kDa, more than 80 kDa, more than 70 kDa, more than 60 kDa, more than 50 kDa, more than 40 kDa, more than 30 kDa or more than 20 kDa, and wherein the recombinant enzyme product is obtained in the filtrate of the microfiltration step.

Clause 14: The process according to any of the clauses 1 to 13 wherein for the microfiltration step corresponding to step (f) from clause 1 and according to step (h) from clause 2, a membrane with a size exclusion limit of more than 5 µm, more than 4 µm, more than 3 µm, more than 2 µm, more than 1 µm, more than 0.5 µm, more than 0.4 µm, more than 0.3 µm, more than 0.2 µm, or more than 0.1 µm and wherein the recombinant enzyme product is obtained in the filtrate of the microfiltration step.

Clause 15: The process according to any of the clauses 1 to 14 wherein after the microfiltration step corresponding to step (f) from clause 1 and according to step (h) from clause 2, optionally, an additional ultrafiltration step is applied, which is characterized by the use of a membrane with a size exclusion limit of more than 100 kDa, more than 80 kDa, more than 60 kDa, more than 50 kDa, more than 40 kDa, more than 30 kDa, more than 20 kDa, more than 15 kDa, more than 10 kDa, more than 5 kDa or more than 1 kDa and wherein the recombinant enzyme product is obtained in the retentate of the ultrafiltration step.

Clause 16: The process according to any of the clauses 1 to 15 wherein the solid/liquid separation step corresponding to step (e) from clause 1 and according to step (g) from clause 2, is realized by techniques of centrifugation, filter presses, and/or microfiltration.

Clause 17: The process according to any of the clauses 1 to 16, wherein at least 5, preferably at least 4, more preferably at least 3, even more preferably at least 2 and most preferred at least 1 intracellular protein is/are expressed.

Clause 18: The process according to any one of clauses 1 to 17, wherein the one or more recombinant enzymes expressed from a production strain alone or together make up at least 50%, preferred at least 40%, more preferred at least 30%, even more preferred at least 20% and most preferred at least 10% of the total protein content of the enzyme product.

Clause 19: The process of any one of clauses 1 to 18, wherein the enzyme product is a food enzyme.

Clause 20: The process of any one of clauses 1 to 19, wherein the enzyme product is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases.

Clause 21: The process of any one of clauses 1 to 20, wherein the enzyme product is selected from the group consisting of a.) carbohydrate-modifying enzymes, such as glycosyl hydrolases, glycosyltransferases, polysaccharide lyases, carbohydrate esterases; b.) amino acid, peptide or protein-modifying enzymes, such as aminotransferases, proteases and peptidases; and c.) lipid modifying enzymes such as lipases or phospholipases.

Clause 22: The process of any one of clauses 1 to 21, wherein the enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

Clause 23: The process of any one of clauses 1 to 22, wherein the microbial production host is modified by deletion of one or more additional genes selected from the group consisting of, for example, the genes encoding the enzymes, preferably the E. coli enzymes, phophosglucomutase, alkaline phosphatase, glucose-1-phosphate phosphatase, UDP-glucose 6-dehydrogenase, cellulose synthase (UDP-forming), alpha,alpha-trehalose-phosphate synthase (UDP-forming), UDP-glucose-hexose-1-phosphate uridylyltransferase, UTP-glucose-1-phosphate uridylyl-transferase, UTP-glucose-1-phosphate uridylyltransferase, UDP-sugar diphosphatase, nucleotide diphosphatase, UDP-glucose 4-epimerase, ribonucleoside-diphosphate reductase, ribonucleoside-diphosphate reductase, lipopolysaccharide N-acetylmannosaminouronosyltransferase, lipid-A-disaccharide synthase, undecaprenyldiphospho-muramoylpentapeptide beta-N-acetylglucosaminyltransferase, undecaprenyl-phosphate 4-deoxy-4-formamido-L-arabinose transferase, 6-phosphofructokinase, pyruvate kinase, uridine kinase, UMP kinase, nucleoside-diphosphate kinase, polyribonucleotide nucleotidyltransferase, UDP-N-acetylglucosamine 2-epimerase (non-hydrolysing), beta-galactosidase, N-acetylneuraminate lyase, N-acetylmannosamine kinase, putative N-acetylmannosamine-6-phosphate 2-epimerase, alpha-galactosidase, galactoside O-acetyltransferase.

Clause 24: The process of any one of clauses 1 to 23, wherein the process comprises the following steps: a.) treatment of a cell disruption crude lysate containing recombinant enzyme products with a nuclease; b.) addition of a precipitation agent to complex nucleic acids; c.) liquid/solid separation to remove cell debris and nucleic acid/precipitation agent complexes from the liquid phase; and d.) conducting a microfiltration step to remove residual solids, and/or high molecular weight components.

Clause 25: A preparation of an enzyme manufactured according to any one of the clauses 1 to 24, which is characterized by a residual DNA concentration of between 0.01 ng/g and 50 ng/g, of between 0.01 ng/g and 40 ng/g, of between 0.01 ng/g and 30 ng/g, of between 0.01 ng/g and 20 ng/g, of between 0.01 ng/g and 10 ng/g, of between 0.01 ng/g and 9 ng/g, of between 0.01 ng/g and 8 ng/g, of between 0.01 ng/g and 7 ng/g, of between 0.01 ng/g and 6 ng/g, of between 0.01 ng/g and 5 ng/g, of between 0.01 ng/g and 4 ng/g, of between 0.01 ng/g and 3 ng/g, of between 0.01 ng/g and 2 ng/g, of between 0.01 ng/g and 1 ng/g, and more preferably of between 0.01 ng/g and 0.9 ng/g, of between 0.01 ng/g and 0.8 ng/g, of between 0.01 ng/g and 0.7 ng/g, of between 0.01 ng/g and 0.6 ng/g, of between 0.01 ng/g and 0.5 ng/g, of between 0.01 ng/g and 0.4 ng/g, of between 0.01 ng/g and 0.3 ng/g, of between 0.01 ng/g and 0.2 ng/g, of between 0.01 ng/g and 0.1 ng/g, or most preferably of below 0.1 ng/g, or utmost preferably of below 0.01 ng/g. The recombinant DNA concentration is to be determined by a method based on a polymerase chain reaction based amplification of a representative DNA fragment comprising recombinant DNA of a size of at least 100 base pairs. The calibration is done with a total DNA preparation from the production host.

Clause 26: A preparation of an enzyme manufactured according to any one of the clauses 1 to 24 wherein the enzyme product is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases.

Clause 27: A preparation of an enzyme manufactured according to any one of the clauses 1 to 24 wherein the enzyme product is selected from the group consisting of a.) carbohydrate-modifying enzymes, such as glycosyl hydrolases, glycosyltransferases, polysaccharide lyases, carbohydrate esterases; b.) amino acid, peptide or protein-modifying enzymes, such as aminotransferases, proteases and peptidases; and c.) lipid modifying enzymes such as lipases or phospholipases.

Clause 28: A preparation of an enzyme manufactured according to any one of the clauses 1 to 24 wherein the enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

Clause 29: An enzyme preparation of a recombinant intracellularly expressed enzyme product with a recombinant DNA concentration of less than 50 ng/g, which contains at least 3 different intracellular host cell proteins of the production host which make up at least 10% of the total protein content of the enzyme preparation.

Clause 30: The enzyme preparation according to clause 29 in which the production host is *Escherichia coli*.

Clause 31: The enzyme preparation according to clause 30, wherein the enzyme preparation contains the expressed enzyme product and in addition contains detectable amounts of a nuclease with an identity of at least 70% to the nuclease of SEQID No:1 or SEQ ID NO:2.

Clause 32: The enzyme preparation according to any of the clauses 29 to 31 in which the recombinant enzyme is selected from the group consisting of oxidoreductases, transferases, hydrolases, lyases, isomerases, and ligases, and preferably is selected from the group consisting of alcohol dehydrogenases, glucose oxidases, sulfhydryl oxidases, aminotransferases, glycosyltransferases, phosphorylases, peptidases, transglutaminases, nitrilases, lipases, asparaginases, phospholipases, glucoamylases, amylases, xylanases, proteases, peptidases, pectinases, cellulases, beta-glucanases esterases, tannases, ureases, cellulases, decarboxylases, and xylose isomerases.

Clause 33: The enzyme preparation according to any of the clauses 29 to 32 in which the recombinant enzyme product is selected from the group consisting of a.) carbohydrate-modifying enzymes, such as glycosyl hydrolases, glycosyltransferases, polysaccharide lyases, carbohydrate esterases; b.) amino acid, peptide or protein-modifying enzymes, such as aminotransferases, proteases and peptidases; and c.) lipid modifying enzymes such as lipases or phospholipases.

Clause 34: The enzyme preparation according to any of the clauses 29 to 33 in which the recombinant enzyme product is a carbohydrate-modifying enzyme and belongs to at least one of the following enzyme classes: sugar phosphorylase, sucrose phosphorylase, trehalose phosphorylase, cellobiose phosphorylase, glycosyl-transferase, i.e. UDP-glycosyl-transferase, glucosyl-transferase, sucrose synthase, galactosyl-transferase, fucosyl-transferase, sialyl-transferase, acetyl-glucosamine-transferase or N-acetyl-galactosyl-transferase.

The following examples further illustrate the invention but are not to be construed as limiting its scope.

Example 1—Processing of a Recombinant Enzyme Product with Composition I

A crude cell extract of recombinant sucrose synthase from *Arabidopsis thaliana* (NCBI Reference Sequence: NP_197583.1, SEQ ID NO:3) is prepared by homogenization of biomass of the recombinant expression host LE1B109, carrying the sucrose synthase gene encoded on the expression plasmid pLE1A27, a derivative of well-known vector pRSF-1b, and expressing the sucrose synthase intracellularly. The biomass to be homogenized is a concentrated cells preparation obtained by concentration of the fermentation broth adjusted to a biomass equivalent of 600 g/L. After homogenization composition I is obtained.

This Composition I is divided into separate fractions, from which each fraction is independently submitted to one of the following process treatments corresponding to the process steps according to the first aspect of the invention in the indicated numerical order:

| Fraction No: | Nuclease treatment Step (ii) | Precipitation and solid/liquid separation Steps (iii)/(iv) | Microfiltration Step (v) |
| --- | --- | --- | --- |
| 1 | 1. | 2. | 3. |
| 2 | — | 1. | 2. |
| 3 | 1. | — | 2. |
| 4 | 1. | 2. | — |
| 5 | 2. | 1. | 3. |
| 6 | 3. | 1. | 2. |

In brief, for Fraction No: 1, composition I is diluted by addition of 15 mM $MgCl_2$ to a final concentration of 5 mM $MgCl_2$. The diluted composition I is supplemented with NuCLEANase (c-LEcta GmbH, Leipzig) to a final concentration of 200 U/g to 300 U/g biomass equivalent and incubated at room temperature or 25° C. for 6 hours. The preparation is diluted by two-fold and supplemented with a suitable precipitation agent from the group of polyethylenimine Lupasol®, or any positively charged precipitation agent from the Superfloc® series to a final concentration of from 0.1% to 2% (w/v) in the preparation. The preparation is incubated at room temperature for 30 minutes to 90 minutes. The solution then is centrifuged at 12.000×g for 60 minutes for separation of solid and liquid phases. The liquid phase is isolated and subjected to a microfiltration using a depth filter with a cut-off of 0.1-0.8 μm at room temperature. The preparation is then together with all other fractions obtained prepared for further analysis as indicated below.

In brief, for Fraction No: 2, composition I is diluted by three-fold and thereby adjusted to a final concentration of 5 mM $MgCl_2$. The preparation is supplemented with a suitable precipitation agent from the group of polyethylenimine Lupasol®, or any positively charged precipitation agent from the Superfloc® series to a final concentration of from 0.1% to 2% (w/v) in the preparation. The preparation is incubated at room temperature for 30 minutes to 90 minutes. The solution then is centrifuged at 12.000×g for 60 minutes for separation of solid and liquid phases. The liquid phase is isolated and subjected to a microfiltration using a depth filter with a cut-off of 0.1-0.8 μm at room temperature. The preparation is then together with all other fractions obtained prepared for further analysis as indicated below.

In brief, for Fraction No: 3, composition I is diluted by addition of 15 mM $MgCl_2$ to a final concentration of 5 mM $MgCl_2$. The diluted composition I is supplemented with NuCLEANase (c-LEcta GmbH, Leipzig) to a final concentration of from 200 U/g to 300 U/mg biomass equivalent and incubated at room temperature or 25° C. for 6 hours. The preparation is diluted by two-fold. The preparation then is centrifuged at 12.000×g for 60 minutes for separation of solid and liquid phases. The liquid phase is isolated and subjected to a microfiltration using a depth filter with a cut-off of 0.1-0.8 μm at room temperature. The preparation then is then together with all other fractions obtained prepared for further analysis as indicated below.

In brief, for Fraction No: 4, composition I is diluted by addition of 15 mM $MgCl_2$ to a final concentration of 5 mM $MgCl_2$. The diluted composition I is supplemented with NuCLEANase (c-LEcta GmbH, Leipzig) to a final concentration of from 200 U/g to 300 U/mg biomass equivalent and incubated at room temperature or 25° C. for 6 hours. The preparation is diluted by two-fold and supplemented with a suitable precipitation agent from the group of polyethylenimine Lupasol®, or any positively charged precipitation agent from the Superfloc® series to a final concentration of from 0.1% to 2% (w/v) in the preparation. The preparation is incubated at room temperature for 30 minutes to 90 minutes. The solution then is centrifuged at 12.000×g for 60 minutes for separation of solid and liquid phases. The preparation then is then together with all other fractions obtained prepared for further analysis as indicated below.

In brief, for Fraction No: 5, composition I is diluted by three-fold. The preparation is supplemented with a suitable precipitation agent from the group of polyethylenimine Lupasol®, or any positively charged precipitation agent from the Superfloc® series to a final concentration of from 0.1% to 2% (w/v) in the preparation. The preparation is incubated at room temperature for 30 minutes to 90 minutes. The solution then is centrifuged at 12.000×g for 60 minutes for separation of solid and liquid phases. The liquid phase is adjusted to a final concentration of 5 mM $MgCl_2$ using 100 mM $MgCl_2$, then is supplemented with NuCLEANase (c-LEcta GmbH, Leipzig) to a final concentration of from 200 U/g to 300 U/mg biomass equivalents and incubated at room temperature or 25° C. for 6 hours. The liquid phase is isolated and subjected to a microfiltration using a depth filter with a cut-off of 0.1-0.8 μm at room temperature. The preparation is then together with all other fractions obtained prepared for further analysis as indicated below.

In brief, for Fraction No: 6, composition I is diluted by three-fold and thereby adjusted to a final concentration of 5 mM $MgCl_2$. The preparation is supplemented with a suitable precipitation agent from the group of polyethylenimine Lupasol®, or any positively charged precipitation agent from the Superfloc® series to a final concentration of from 0.1% to 2% (w/v) in the preparation. The preparation is incubated at room temperature for 30 minutes to 90 minutes. The solution then is centrifuged at 12.000×g for 60 minutes for separation of solid and liquid phases. The liquid phase is isolated and subjected to a microfiltration using a depth filter with a cut-off of 0.1-0.8 μm at room temperature. The liquid phase then is supplemented with NuCLEANase (c-LEcta GmbH, Leipzig) to a final concentration of from 200 U/g biomass equivalents to 300 U/mg biomass equivalents and incubated at room temperature or 25° C. for 6 hours. The preparation is then together with all other fractions obtained prepared for further analysis as indicated below.

All enzyme preparations obtained from Fractions NO: 1 to Fraction NO: 6 are further processed according to the same protocols in order to adjust the final preparation volumes in order to assure comparative analysis. Processing is accomplished by submitting the samples to an ultrafiltration step using an exclusion size of 30 kDa and concentrated about five- to ten-fold up to an adjusted volume of all fractions. Alternatively, the enzyme preparations obtained from Fractions NO: 1 to Fraction NO: 6 are processed by freeze-drying of comparable volume amounts of each fraction and re-dissolving the lyophilizates in identical volumes of a buffer suitable for subsequent DNA and activity analysis.

The final recombinant enzyme preparations obtained from processed Fractions NO: 1 to Fraction NO: 6 are subjected to DNA detection using PCR technology with two oligonucleotide primers directed towards the microbial host DNA.

In addition the recombinant enzyme formulations of the intermediate preparations or final preparations obtained from the processing of the individual factions are analyzed for enzyme activity using a coupled photometric assay that measures the non-hydrolytic breakdown of sucrose into fructose and UDP-activated glucose (UDP-glucose) by sucrose synthase. The formed fructose is detected in a coupled reaction with hexokinase (HK), phosphoglucose isomerase (PGI), and glucose-6-phosphate dehydrogenase (G6P-DH). The NADPH formed in the G6P-DH reaction is measured by a photometric detection at 340 nm.

The results are shown in the following Table:

| Fraction No: | Nuclease treatment Step (ii) | Precipitation and solid/liquid separation Steps (iii)/(iv) | Micro-filtration Step (v) | Recovery of catalytic activity [% compared to Composition I] | DNA content [ng/g final product] |
|---|---|---|---|---|---|
| 1 | 1. | 2. | 3. | 87% | <0.1 ng/g |
| 2 | — | 1. | 2. | 99% | >10 ng/g |
| 3 | 1. | — | 2. | 84% | >10 ng/g |
| 4 | 1. | 2. | — | 98% | >1 ng/g |
| 5 | 2. | 1. | 3. | 89% | >10 ng/g |
| 6 | 3. | 1. | 2. | 91% | >10 ng/g |

As is obvious from the results, the process treatment of Fraction 1 is superior to the other process treatments.

Example 2—Expression and Formulation of Sucrose Synthase of Wildtype *Arabidopsis thaliana*

The gene coding for the sucrose synthase of wildtype *Arabidopsis thaliana* (NCBI Reference Sequence: NP_197583.1, SEQ ID NO:3) is cloned into the expression vector pLE1A17 (derivative of pRSF-1b, Novagen). The resulting plasmid is used for transformation of *E. coli* BL21 (DE3) cells.

Cells are cultivated in ZYM505 medium (F. William Studier, Protein Expression and Purification 41 (2005) 207-234) supplemented with kanamycin (50 mg/l) at 37° C. Expression of the genes is induced at logarithmic phase by IPTG (0.2 mM) and carried out at 30° C. and 200 rpm for 16-18 hours.

Cells are harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells are then disrupted by sonication. The preparation then is supplemented with a suitable precipitation agent from the group of polyethylenimine Lupasol®, or any positively charged precipitation agent from the Superfloc® series to a final concentration of from 0.1% to 2% (w/v) in the preparation. The crude extracts are separated from cell debris by centrifugation (18000×g 40 min, 4° C.). The supernatant is sterilized by filtration through a 0.2 μm filter, resulting in an enzymatic active preparation.

Example 3—Expression and Formulation of UDP-Glycosyltransferase of Wildtype *Solanum lycopersicum*

The gene coding for the UDP-glycosyltransferase of wildtype *Solanum lycopersicum* (UGTSL2) (GenBank accession no. XP_004250485.1, SEQ ID NO:5) is cloned into the expression vector pLE1A17 (derivative of pRSF-1b, Novagen). The resulting plasmid is used for transformation of *E. coli* BL21(DE3) cells.

Cells are cultivated in ZYM505 medium (F. William Studier, Protein Expression and Purification 41 (2005) 207-234) supplemented with kanamycin (50 mg/l) at 37° C. Expression of the genes is induced at logarithmic phase by IPTG (0.1 mM) and carried out at 30° C. and 200 rpm for 16-18 hours.

Cells are harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells are then disrupted by sonication. The preparation then is supplemented with a suitable precipitation agent from the group of polyethylenimine Lupasol®, or any positively charged precipitation agent from the Superfloc® series to a final concentration of from 0.1% to 2% (w/v) in the preparation. The crude extracts are separated from cell debris by centrifugation (18000×g 40 min, 4° C.). The supernatant is sterilized by filtration through a 0.2 μm filter, resulting in an enzymatic active preparation.

Example 4—Expression and Formulation of Glycosyltransferase of Wildtype *Stevia rebaudiana*

The gene coding for the glycosyltransferase of wildtype *Stevia rebaudiana* (UGT76G1) (GenBank accession no. AAR06912.1 SEQ ID NO:4) is cloned into the expression vector pLE1A17 (derivative of pRSF-1b, Novagen). The resulting plasmid is used for transformation of *E. coli* BL21 (DE3) cells.

Cells are cultivated in ZYM505 medium (F. William Studier, Protein Expression and Purification 41 (2005) 207-234) supplemented with kanamycin (50 mg/l) at 37° C. Expression of the genes is induced at logarithmic phase by IPTG (0.1 mM) and carried out at 30° C. and 200 rpm for 16-18 hours.

Cells are harvested by centrifugation (3220×g, 20 min, 4° C.) and re-suspended to an optical density of 200 (measured at 600 nm ($OD_{600}$)) with cell lysis buffer (100 mM Tris-HCl pH 7.0; 2 mM $MgCl_2$, DNA nuclease 20 U/mL, lysozyme 0.5 mg/mL). Cells are then disrupted by sonication. The preparation is supplemented with a suitable precipitation agent from the group of polyethylenimine Lupasol®, or any positively charged precipitation agent from the Superfloc® series to a final concentration of from 0.1% to 2% (w/v) in the preparation. The crude extracts are separated from cell debris by centrifugation (18000×g 40 min, 4° C.). The supernatant is sterilized by filtration through a 0.2 μm filter, resulting in an enzymatic active preparation.

What we claim is:

1. A process for preparing a recombinant enzyme formulation comprising:
   (i) providing a composition I comprising a recombinant enzyme, nucleic acids, and optionally cell debris;
   (ii) adding to the composition I a nuclease wherein the nuclease breaks down the nucleic acids to result in a composition II comprising the recombinant enzyme, broken down nucleic acids, and optionally the cell debris;
   (iii) subsequently, adding to the composition II a precipitation agent for the broken down nucleic acids wherein the broken down nucleic acids are complexed resulting in a composition III comprising the recombinant enzyme, complexed broken down nucleic acids, and optionally the cell debris;
   (iv) optionally, purifying the composition III by solid/liquid separation resulting in a separated solid phase comprising the complexed broken down nucleic acids and optionally the cell debris and a liquid composition IV comprising the recombinant enzyme; and
   (v) subsequently, purifying the composition III or the composition IV by microfiltration resulting in a composition V, the recombinant enzyme formulation, comprising the recombinant enzyme.

2. The process according to claim 1, wherein the nuclease is selected from the group consisting of endonucleases, exonucleases, and a combination thereof.

3. The process according to claim 1, wherein the nuclease is has at least 70%, at least 75%, at least 80%, at least 85%, at least 90%, at least 95%, at least 98%, or at least 99%, sequence identity to SEQ ID NO:1 or SEQ ID NO:2.

4. The process according to claim 1, wherein in (ii) the nuclease is added in an amount of from 50 U to 2000 U, from 50 U to 1000 U, from 50 U to 500 U, from 1000 to 300 U, from 150 U to 300 U, or and preferably of from 200 U to 300 U per gram biomass equivalent of composition II.

5. The process according to claim 1, wherein the recombinant enzyme
   (a) is selected from one or more of the group consisting of oxidoreductases, transferases, hydrolases, lyases, isomerases, and ligases; or
   (b) is selected from one or more of the group consisting of (b-1) carbohydrate-modifying enzymes, (b-2) amino acid, peptide or protein-modifying enzymes and (b-3) lipid modifying enzymes; or
   (c) is a carbohydrate-modifying enzyme and belongs to at least one of the following enzyme classes: sugar phosphorylase, sucrose phosphorylase, trehalose phosphorylase, cellobiose phosphorylase, glycosyl-transferase; or is a combination of any one of (a)-(c).

6. The process according to claim 5, wherein the recombinant enzyme is a wild-type enzyme or a variant derived therefrom by enzyme engineering technologies.

7. The process according to claim 1, wherein the precipitation agent is a cationic polymer.

8. The process according to claim 7, wherein the precipitation agent is selected from the group consisting of chitosan; polyamines; polyamino acids; and polyacrylamides.

9. The process according to claim 8, wherein the precipitation agent is a polyamine selected from the group consisting of polyallylamine, polyvinylamine, polyethylenimine, and poly-N-methylvinylamine, or, wherein the precipitation agent is a polyamino acid selected from polyarginine and polylysine.

10. The process according to claim 7, wherein the precipitation agent is selected from the group consisting of polyethylenimines and polydiallyldimethyl ammonium chloride.

11. The process according to claim 1, wherein the precipitation agent is or comprises a one or more flocculants selected from the group consisting of
   cationic polyamine-based flocculants;
   cationic polyacrylamide-based flocculants;
   anionic polyamine based flocculants;
   ammonium sulfate; and
   calcium chloride.

12. The process according to claim 1, wherein the recombinant enzyme
   is selected from the group consisting of alcohol dehydrogenases, glucose oxidases, sulfhydryl oxidases, aminotransferases, glycosyl-transferases, phosphorylases, peptidases, transglutaminases, nitrilases, lipases, aspara-ginases, phospholipases, glucoamylases, amylases, xylanases, proteases, peptidases, pectinases, cellulases, beta-glucanases esterases, tannases, ureases, cellulases, decarboxylases, and xylose isomerases; or
   is selected from the group consisting of glycosyl hydrolases, glycosyltransferases, polysaccharide lyases, carbohydrate esterases; aminotransferases, proteases, peptidases; lipases and phospholipases; or
   is selected from the group consisting of UDP-glycosyl-transferase, glucosyl-transferase, sucrose synthase, galactosyl-transferase, fucosyl-transferase, sialyl-transferase, acetyl-glucosamine-transferase and N-acetyl-galactosyl-transferase.

13. The process according to claim 11, wherein the precipitation agent is or comprises a compound selected from the group consisting of
   dimethylamine-epichlorohydrin copolymer, methylamine-epichlorohydrin copolymer, and dimethylamine-epichlorohydrin-ethylenediamine terpolymer,
   polyacrylamide modified by condensation with formaldehyde and dimethylamine and acrylamide-acryloxy-ethyl-trimethyl-ammonium chloride copolymer,
   acrylamide-acrylic acid copolymer,
   ammonium sulfate, and
   calcium chloride.

14. The process according to claim 1, wherein during the microfiltration in (v)
   a) residual solids,
   b) components having a molecular weight that exceeds that of the recombinant enzyme,
   or
   a) and b) are removed.

15. The process according to claim 1, wherein a membrane or a depth-filter is used for the microfiltration in (v), wherein the composition V is a filtrate of the microfiltration in (v).

16. The process according to claim 15, wherein the membrane is used for the microfiltration in (v) and the membrane has a size exclusion limit of
   more than 1000 kDa, more than 300 kDa, more than 150 kDa, more than 50 kDa, or more than 20 kDa; or
   more than 5μm, more than 3 μm, more than 0.3 μm, or more than 0.1 μm.

17. The process according to claim 16, wherein the membrane has a size exlusion limit of more than 1000 kDa, more than 300 kDa, more than 150 kDa, more than 50 kDa, or more than 20 kDa.

18. The process according to claim 15, wherein the membrane is used for the microfiltration in (v) and the membrane has a size exclusion limit of more than 5 µm, more than 4 µm, more than 3 µm, more than 2 µm, more than 1 µm, more than 0.5 µm, more than 0.4 µm, more than 0.3 µm, more than 0.2 µm, or more than 0.1 µm.

19. The process according to claim 18, wherein the membrane has a size exclusion limit of more than 5 µm, more than 3 µm, more than 0.3 µm, or more than 0.1 µm.

20. The process according to claim 14, wherein the microfiltraiton in (v) involves removal of residual solids.

21. He process according to claim 1, wherein the microfiltration in (v) involves
- a) a membrane having a size exlusion limit of
- more than 1000 kDa, more than 500 kDa, more than 400 kDa, more than 300 kDa, more than 200 kDa, more than 150 kDa, more than 100 kDa, more than 90 kDa, more than 80 kDa, more than 70 kDa, more than 60 kDa, more than 50 kDa, more than 40 kDa, more than 30 kDa, or more than 20 kDa; or
- more than 5 µm, more than 4 µm, more than 3 µm, more than 2 µm, more than 1 µm, more than 0.5 µm, more than 0.4 µm, more than 0.3 µm, more than 0.2 µm, or more than 0.1 µm; or
- b) a filter with equivalent molecular weight exclusion properties,
- wherein the composition V is a filtrate of the microfiltration.

* * * * *

UNITED STATES PATENT AND TRADEMARK OFFICE
CERTIFICATE OF CORRECTION

PATENT NO. : 11,286,474 B2
APPLICATION NO. : 16/682511
DATED : March 29, 2022
INVENTOR(S) : Schoenert et al.

It is certified that error appears in the above-identified patent and that said Letters Patent is hereby corrected as shown below:

On the Title Page

On Page 2, Item (56), in Column 1, under "OTHER PUBLICATIONS", Line 10, delete "S" and insert -- S. --, therefor.

In the Specification

In Column 23, Lines 49-50, delete "phophosglucomutase," and insert -- phosphoglucomutase, --, therefor.

In Column 24, Line 20, delete "phophosglucomutase," and insert -- phosphoglucomutase, --, therefor.

In Column 34, Line 39, delete "phophosglucomutase," and insert -- phosphoglucomutase, --, therefor.

In the Claims

In Column 53, in Claim 4, Line 38, delete "or and preferably" and insert -- or --, therefor.

In Column 54, in Claim 11, Line 6, delete "a one" and insert -- one --, therefor.

In Column 54, in Claim 17, Line 63, delete "exlusion" and insert -- exclusion --, therefor.

In Column 55, in Claim 20, Line 9, delete "microfiltraiton" and insert -- microfiltration --, therefor.

In Column 55, in Claim 21, Line 10, delete "He" and insert -- The --, therefor.

In Column 55, in Claim 21, Line 11, delete "involves" and insert -- involves using --, therefor.

In Column 55, in Claim 21, Line 12, delete "exlusion" and insert -- exclusion --, therefor.

Signed and Sealed this
Thirteenth Day of September, 2022

Katherine Kelly Vidal
*Director of the United States Patent and Trademark Office*

CERTIFICATE OF CORRECTION (continued)
U.S. Pat. No. 11,286,474 B2

In Column 55, in Claim 21, Lines 25-26, delete "microfilitration." and insert -- microfiltration. --, therefor.